(12) United States Patent
Combs et al.

(10) Patent No.: US 10,144,798 B2
(45) Date of Patent: Dec. 4, 2018

(54) METHODS FOR DESIGNING POLYISOCYANURATE FOAM-FORMING COMPOSITIONS, RELATED POLYISOCYANURATE FOAM-FORMING COMPOSITIONS, AND FOAMS PRODUCED THEREBY

(71) Applicant: Covestro LLC, Pittsburgh, PA (US)

(72) Inventors: George Combs, McMurray, PA (US); Gerald W. Phelan, McMurray, PA (US)

(73) Assignee: COVESTRO LLC, Pittsburgh, PA (US)

( * ) Notice: Subject to any disclaimer, the term of this patent is extended or adjusted under 35 U.S.C. 154(b) by 0 days.

(21) Appl. No.: 14/976,650

(22) Filed: Dec. 21, 2015

(65) Prior Publication Data
US 2017/0174821 A1    Jun. 22, 2017

(51) Int. Cl.
| | |
|---|---|
| *C08G 18/76* | (2006.01) |
| *G01N 25/18* | (2006.01) |
| *C08J 9/14* | (2006.01) |
| *C08G 18/08* | (2006.01) |
| *C08G 18/42* | (2006.01) |

(Continued)

(52) U.S. Cl.
CPC .......... *C08G 18/7664* (2013.01); *B32B 5/18* (2013.01); *B32B 27/065* (2013.01); *B32B 27/40* (2013.01);
(Continued)

(58) Field of Classification Search
CPC .................................................. G01N 25/18
See application file for complete search history.

(56) References Cited

U.S. PATENT DOCUMENTS

| | | |
|---|---|---|
| 4,572,865 A | 2/1986 | Gluck et al. |
| 8,106,106 B2 | 1/2012 | Letts |

(Continued)

OTHER PUBLICATIONS

Bogdan, M.; Hoerter, J.; Moore, F. O. Meeting the insulation requirements of the building envelope with polyurethane and polyisocyanurate foam. Journal of Cellular Plastics, 2005, vol. 41, pp. 41-56.*

(Continued)

*Primary Examiner* — Stephen E Rieth
(74) *Attorney, Agent, or Firm* — Donald R. Palladino

(57) ABSTRACT

Disclosed are methods for designing a polyisocyanurate foam-forming composition with good low temperature insulation performance. The methods include: (a) measuring the LTTR of a first polyisocyanurate faced foam laminate prepared from a first polyisocyanurate foam-forming composition comprising a blowing agent composition, wherein the LTTR is measured at a plurality of temperatures to identify a calculated inflection point temperature below which defines a first mathematical correlation between temperature and the LTTR of the first polyisocyanurate faced foam laminate and above which defines a second mathematical correlation between temperature and the LTTR of the first polyisocyanurate faced foam laminate; (b) identifying a plurality of predicted mathematical correlations between temperature and the LTTR of the first polyisocyanurate faced foam laminate at a plurality of reduced inflection point temperatures below the calculated inflection point temperature; and (c) using the plurality of predicted mathematical correlations identified in step (b) to design a second polyisocyanurate foam-forming composition that comprises a blowing agent composition and produces a second polyisocyanurate faced foam laminate that has a LTTR satisfying a threshold value at all mean insulation temperatures within a temperature range of 10° F. to 75° F. (−12.2° C. to 23.9° C.).

19 Claims, 8 Drawing Sheets

(51) Int. Cl.

| | | |
|---|---|---|
| B32B 5/18 | (2006.01) | |
| B32B 27/06 | (2006.01) | |
| B32B 27/40 | (2006.01) | |
| C08G 18/09 | (2006.01) | |
| E04C 2/20 | (2006.01) | |
| C08G 18/16 | (2006.01) | |
| C08G 18/18 | (2006.01) | |
| C08G 18/22 | (2006.01) | |
| C08G 101/00 | (2006.01) | |

(52) U.S. Cl.
CPC ......... *C08G 18/092* (2013.01); *C08G 18/163* (2013.01); *C08G 18/1808* (2013.01); *C08G 18/225* (2013.01); *C08G 18/42* (2013.01); *C08J 9/141* (2013.01); *E04C 2/205* (2013.01); *G01N 25/18* (2013.01); *C08G 2101/00* (2013.01); *C08G 2101/005* (2013.01); *C08G 2101/0025* (2013.01); *C08G 2105/02* (2013.01); *C08J 2203/14* (2013.01); *C08J 2203/182* (2013.01); *C08J 2205/10* (2013.01); *C08J 2375/06* (2013.01)

(56) References Cited

U.S. PATENT DOCUMENTS

| 2004/0162359 | A1 | 8/2004 | Barber et al. |
| 2011/0269860 | A1 | 11/2011 | Creazzo et al. |
| 2014/0066532 | A1 | 3/2014 | Combs et al. |
| 2014/0094530 | A1 | 4/2014 | Combs et al. |

OTHER PUBLICATIONS

Eilbracht, C.; Schiller, C.; Metz, T.; Tauchen, R. Understanding the relationship between surfactants and aged insulation value of PIR foam. Polyurethanes Technical Conference, Atlanta GA, Sep. 24-26, 2012.*

Graham, Mark S.; "Testing R-values"; Tech Today; Mar. 2015; p. 14; www.professionalroofing.net.

Graham, Mark S.; "R-value concerns"; Tech Today; May 2010; p. 24; www.professionalroofing.net.

Graham, Mark S.; "Revised R-values"; Tech Today; Dec. 2010; p. 20; www.professionalroofing.net.

Dupont; Formacel Foam Expansion Agent; Technical Information ABA-14; Temperature Effect on the Insulation Value of Polyurethane Foams; 2011 Dupont; formacel.dupont.com.

Fleurent, Hilde and Thijs, Sonja; "The Use of Pentanes as Blowing Agent in Rigid Polyurethane Foam"; Journal of Cellular Plastics; vol. 31; Nov. 1995; pp. 580-599.

Pedersen, C. O.; "Advanced Zone Simulation in EnergyPlus: Incorporation of Variable Properties and Phase Change Material (PCM) Capability"; University of Illinois at Urbana-Champaign, Urbana IL, USA; Proceedings:Building Simulation 2007; pp. 1341-1345.

Tabares-Velasco, Paulo Cesar et al; "Verification and Validation of EnergyPlus Conduction Finite Difference and Phase Change Material Models for Opaque Wall Assemblies"; NREL National Renewable Energy Laboratory; Technical Report NREL/TP-5500-55792; Jul. 2012.

Singh, Sachchida N. et al; "Long Term Thermal Resistance of Pentane Blown Polyisocyanurate Laminate Boards"; Journal of Cellular Plastics; vol. 39; Sage Publications; pp. 265-280; Jul. 1, 2003.

Building Science Corporation; BSC Information Sheet 502; "Understanding the Temperature Dependence of R-values for Polyisocyanurate Roof Insulation"; buildingscience.com; Apr. 12, 2013.

Saunders, J.H., and Frisch, K.C.: Polyurethanes Chemistry and Technology; Part II Technology; VIII, Rigid Foams; Interscience Publishers; Copyright 1964 by John Wiley & Sons, Inc.; pp. 251-298.

* cited by examiner

METHODS FOR DESIGNING POLYISOCYANURATE FOAM-FORMING COMPOSITIONS, RELATED POLYISOCYANURATE FOAM-FORMING COMPOSITIONS, AND FOAMS PRODUCED THEREBY

FIELD

The present invention is directed to, among other things, methods for designing a polyisocyanurate foam-forming composition with good low temperature insulation performance, polyisocyanurate foam-forming compositions produced by such methods, and foams produced from such compositions.

BACKGROUND

Insulation plays an important role in the energy efficiency and environmental impact of building envelopes. In many cases, polyisocyanurate foam is used for building insulation as it has many advantages, such as relatively low installed cost, good fire resistance and high thermal resistance. As a result, it is important to understand the thermal resistance performance of such foam insulation.

In order to allow for a simple, yet consistent methodology to measure and compare thermal performance, North American manufacturers of building envelope thermal insulation test and report the R-value (a measure of thermal resistance used in the building and construction industry) of their products in compliance with industry standards. Long term thermal resistance ("LTTR") is an industry measure representing R-value of building insulation comprised of a cellular plastic insulation that contains gases other than air where the composition of the retained gases changes with time. Often, a LTTR of at least 5.4 $ft^2 \cdot hr \cdot °F./BTU \cdot inch$ (0.936 $m^2 \cdot °C./W@25$ mm) is desirable and a minimum design value of 5.7 $ft^2 \cdot hr \cdot °F./BTU \cdot inch$ (0.988 $m^2 \cdot °C./W@25$ mm) has been suggested by the Polyisocyanurate Manufacturers Association (PIMA). A problem with this standard, however, is that it requires measurement of R-value at a mean temperature of 75° F. (23.9° C.). Such a representation of R-value does not reflect performance of foam insulation across the full range of exposure temperatures.

A problem that has been associated with polyisocyanurate foam building insulation is that, unlike some other insulation materials, it has been reported that such insulation exhibits poorer thermal resistance, i.e., reduced R-value, at low temperatures. As a result, it would be desirable to provide methods for designing polyisocyanurate foam-forming compositions that produce a faced rigid foam laminate having a LTTR of at least 5.4 $ft^2 \cdot hr \cdot °F./BTU \cdot inch$ ((0.936 $m^2 \cdot °C./W@25$ mm) at all mean insulation temperatures within the range of from 10° F. to 75° F. (−12.2° C. to 23.9° C.), when measured according to CAN/UL S770-09. The present invention was made in view of the foregoing desire.

SUMMARY OF THE INVENTION

In certain respects, the present invention is directed to methods for designing a polyisocyanurate foam-forming composition. These methods comprise: (a) measuring the LTTR of a first polyisocyanurate faced foam laminate prepared from a first polyisocyanurate foam-forming composition comprising a blowing agent composition comprising one or more hydrocarbon blowing agents with an atmospheric pressure boiling point of at least 68° F. (20° C.), wherein the LTTR is measured according to CAN/UL S770-09 at a plurality of temperatures to identify a calculated inflection point temperature below which defines a first mathematical correlation between temperature and the LTTR of the first polyisocyanurate faced foam laminate and above which defines a second mathematical correlation between temperature and the LTTR of the first polyisocyanurate faced foam laminate; (b) identifying a plurality of predicted mathematical correlations between temperature and the LTTR of the first polyisocyanurate faced foam laminate at a plurality of reduced inflection point temperatures below the calculated inflection point temperature; and (c) using the plurality of predicted mathematical correlations to design a second polyisocyanurate foam-forming composition that is different from the first polyisocyanurate foam-forming composition and which comprises a blowing agent composition comprising one or more hydrocarbon blowing agents with an atmospheric pressure boiling point of at least 68° F. (20° C.), wherein the second polyisocyanurate foam-forming composition produces a second polyisocyanurate faced foam laminate that has a LTTR of at least 5.4 $ft^2 \cdot hr \cdot °F./BTU \cdot inch$ (0.936 $m^2 \cdot °C./W@25$ mm) at all mean insulation temperatures within a temperature range of 10° F. to 75° F. (−12.2° C. to 23.9° C.), when measured according to CAN/UL S770-09.

In other respects, the present invention is directed to methods for designing a polyisocyanurate foam-forming composition that comprise: (a) measuring the LTTR of a first polyisocyanurate faced foam laminate prepared from a first polyisocyanurate foam-forming composition comprising a blowing agent composition comprising one or more hydrocarbon blowing agents with an atmospheric pressure boiling point of at least 68° F. (20° C.), wherein the LTTR is measured according to CAN/UL S770-09 at a plurality of temperatures to identify a calculated inflection point temperature below which defines a first mathematical correlation between temperature and the LTTR of the first polyisocyanurate faced foam laminate and above which defines a second mathematical correlation between temperature and the LTTR of the first polyisocyanurate faced foam laminate; (b) identifying a plurality of predicted mathematical correlations between temperature and the LTTR of the first polyisocyanurate faced foam laminate at a plurality of reduced inflection point temperatures below the calculated inflection point temperature; (c) using the plurality of predicted mathematical correlations to determine a predicted inflection point temperature range where heating energy consumption of a selected building type in geographic locations where HDD65 values are greater than 2000 that is insulated with a polyisocyanurate foam insulation would be equal to or lower than the heating energy consumption for the selected building type in the same geographic location that is insulated with a theoretical insulation having a selected constant LTTR, such as a LTTR of 5.77 $ft^2 \cdot hr \cdot °F./BTU \cdot inch$ (1.00 $m^2 \cdot °C./W@25$ mm), at all temperatures within the range of 10° F. to 75° F. (−12.2° C. to 23.9° C.); and (d) using the predicted inflection point temperature to design a second polyisocyanurate foam-forming composition that is different from the first polyisocyanurate foam-forming composition and which comprises a blowing agent composition comprising one or more hydrocarbon blowing agents with an atmospheric pressure boiling point of at least 68° F. (20° C.), wherein the second polyisocyanurate foam-forming composition produces a second polyisocyanurate faced foam laminate that has a LTTR of at least 5.4 $ft^2 \cdot hr \cdot °F./BTU \cdot inch$ (0.936 $m^2 \cdot °C./W@25$ mm) at all mean insulation temperatures within a temperature range of 10° F. to 75° F. (−12.2° C. to 23.9° C.), when measured according to CAN/UL S770-09.

The present invention is also directed to, among other things, polyisocyanurate foam-forming compositions designed by such methods and faced foam laminates prepared from such compositions. In some respects, the present invention is directed to polyisocyanurate faced rigid foam laminates comprising a rigid foam that is the reaction product of a polyisocyanurate foam-forming composition comprising a blowing agent composition comprising one or more hydrocarbon blowing agents with an atmospheric pressure boiling point greater than or equal to 20° C., wherein the blowing agent composition is selected to provide a polyisocyanurate face foam laminate having a LTTR of at least 5.4 ft$^2$·hr·° F./BTU·inch (0.936 m$^2$·° C./W@25 mm) at all mean insulation temperatures within a temperature range of 10° F. to 75° F. (−12.2° C. to 23.9° C.), when measured according to CAN/UL S770-09.

DETAILED DESCRIPTION

Figure 1:
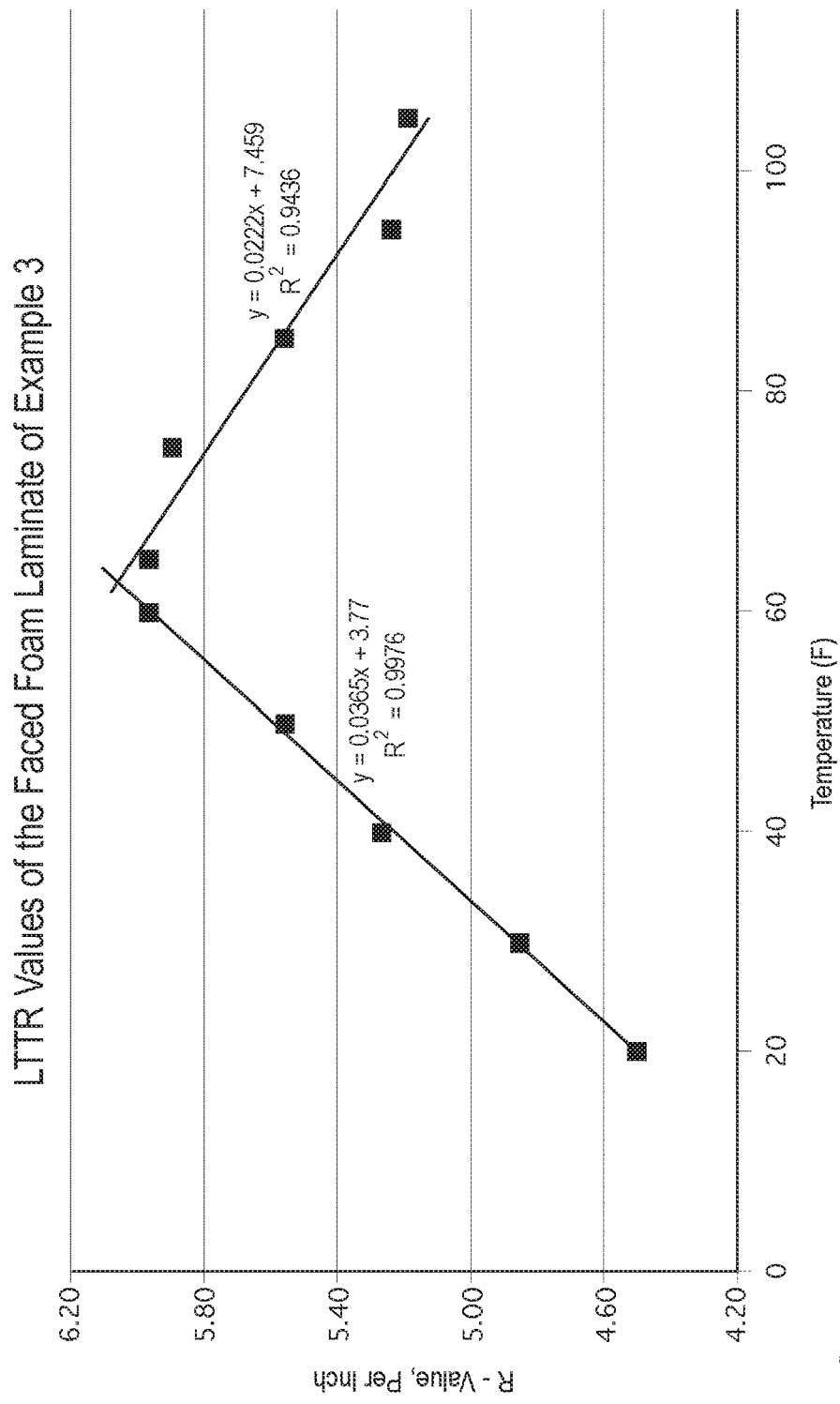
FIG. 1 is a graphical representation of the data of Table 3, which includes mathematical equations determined by a linear fit of the data of Table 3.

Various embodiments are described and illustrated in this specification to provide an overall understanding of the structure, function, properties, and use of the disclosed inventions. It is understood that the various embodiments described and illustrated in this specification are non-limiting and non-exhaustive. Thus, the invention is not limited by the description of the various non-limiting and non-exhaustive embodiments disclosed in this specification. The features and characteristics described in connection with various embodiments may be combined with the features and characteristics of other embodiments. Such modifications and variations are intended to be included within the scope of this specification. As such, the claims may be amended to recite any features or characteristics expressly or inherently described in, or otherwise expressly or inherently supported by, this specification. Further, Applicant(s) reserve the right to amend the claims to affirmatively disclaim features or characteristics that may be present in the prior art. Therefore, any such amendments comply with the requirements of 35 U.S.C. § 112 and 35 U.S.C. § 132(a). The various embodiments disclosed and described in this specification can comprise, consist of, or consist essentially of the features and characteristics as variously described herein.

Any patent, publication, or other disclosure material identified herein is incorporated by reference into this specification in its entirety unless otherwise indicated, but only to the extent that the incorporated material does not conflict with existing definitions, statements, or other disclosure material expressly set forth in this specification. As such, and to the extent necessary, the express disclosure as set forth in this specification supersedes any conflicting material incorporated by reference herein. Any material, or portion thereof, that is said to be incorporated by reference into this specification, but which conflicts with existing definitions, statements, or other disclosure material set forth herein, is only incorporated to the extent that no conflict arises between that incorporated material and the existing disclosure material. Applicant(s) reserves the right to amend this specification to expressly recite any subject matter, or portion thereof, incorporated by reference herein.

In this specification, other than where otherwise indicated, all numerical parameters are to be understood as being prefaced and modified in all instances by the term "about", in which the numerical parameters possess the inherent variability characteristic of the underlying measurement techniques used to determine the numerical value of the parameter. At the very least, and not as an attempt to limit the application of the doctrine of equivalents to the scope of the claims, each numerical parameter described in the present description should at least be construed in light of the number of reported significant digits and by applying ordinary rounding techniques.

Also, any numerical range recited in this specification is intended to include all sub-ranges of the same numerical precision subsumed within the recited range. For example, a range of "1.0 to 10.0" is intended to include all sub-ranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited in this specification is intended to include all lower numerical limitations subsumed therein and any minimum numerical limitation recited in this specification is intended to include all higher numerical limitations subsumed therein. Accordingly, Applicant(s) reserves the right to amend this specification, including the claims, to expressly recite any sub-range subsumed within the ranges expressly recited herein. All such ranges are intended to be inherently described in this specification such that amending to expressly recite any such sub-ranges would comply with the requirements of 35 U.S.C. § 112 and 35 U.S.C. § 132(a).

The grammatical articles "one", "a", "an", and "the", as used in this specification, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and may be employed or used in an implementation of the described embodiments. Further, the use of a singular noun includes the plural, and the use of a plural noun includes the singular, unless the context of the usage requires otherwise.

Unless otherwise indicated by the context, as used herein, the term "mean insulation temperature", when used with reference to measurement of an R-value or thermal conductivity (k-factor) of an insulation material, means the mathematical mean of the two parallel plate temperatures in contact with either surface of the insulation material being tested.

As indicated, certain embodiments of the present invention are directed to methods for designing a polyisocyanurate foam-forming composition.

The methods for designing a polyisocyanurate foam-forming composition of the present invention comprise measuring the LTTR of a first polyisocyanurate faced foam laminate prepared from a first polyisocyanurate foam-forming composition comprising a blowing agent composition comprising one or more hydrocarbon blowing agents with an atmospheric pressure boiling point of at least 68° F. (20° C.).

More particularly, the first polyisocyanurate foam-forming composition used in certain methods of the present invention comprises: (a) an organic polyisocyanate; (b) a polymeric polyol with a nominal functionality of at least 2.0, and (c) a blowing agent composition comprising one or more hydrocarbon blowing agents with an atmospheric pressure boiling point of at least 68° F. (20° C.).

Any of the known organic polyisocyanates can be used in the practice of the present invention. Examples of suitable polyisocyanates include, without limitation, substituted or unsubstituted aromatic, aliphatic, and cycloaliphatic polyisocyanates having at least two isocyanate groups. Polyfunctional aromatic isocyanates are often used. Specific examples of suitable aromatic isocyanates include, but are not limited to, 4,4'-diphenylmethane diisocyanate (MDI), polymeric MDI (pMDI), toluene diisocyanate, allophanate-modified isocyanates, isocyanate-terminated prepolymers and carbodiimide-modified isocyanates. In some embodiments, the organic polyisocyanate comprises pMDI having an average NCO functionality of from 2.2 to 3.3 and a viscosity of from 25 to 2000 mPas and prepolymers thereof prepared with polyols or other oligomers or polymers such as polyether or polyester polyols that contain active hydrogen atoms. In certain embodiments, the pMDI has a functionality of from 2.2 to 3.0 and a viscosity less than about 800 mPas at 25° C. Any mixtures of organic polyisocyanates may, of course, be used.

In certain embodiments, the organic polyisocyanate(s) is/are included in the foam-forming system, i.e., composition, in an amount of at least 50%, such as from 55% to 75%, or, in some cases, from 59% to 69% by weight, based on total weight of the foam-forming composition.

Any material having at least two reactive groups capable of reacting with an isocyanate group is suitable for use in the first polyisocyanurate foam-forming composition. In certain embodiments, the isocyanate-reactive material comprises a polyester polyol (such as an aromatic polyester polyol) and/or a polyether polyol, such as those having an average hydroxyl functionality of from 2 to 8, such as 2 to 6, or, in some cases, 2.0 to 2.5, and/or a hydroxyl number of 100 mg KOH/gm to 1000 mgKOH/gm or, in some cases, 200 mgKOH/gm to 500 mgKOH/gm. In certain embodiments, a blend of an aromatic polyester polyol and a polyester and/or polyether polyol that contains renewable content derived from incorporation of regenerable materials, such as fatty acid triglycerides, sugar, or natural glycerin, is used.

In certain embodiments, the polyol(s) is/are a present in an amount of 10% to 40%, such as 20% to 40%, or, in some cases, 25% to 35% by weight, based on total weight of the foam-forming composition.

In the present invention, the relative amounts of organic polyisocyanate and polymeric polyol(s) used in the first polyisocyanurate foam-forming composition are selected so as to provide the composition with a NCO:OH index of at least 1.8, such as at least 2.0, or, in some cases, 2.0 to 3.0.

As indicated, the first polyisocyanurate foam-forming composition used in certain methods of the present invention comprises a blowing agent composition comprising one or more hydrocarbon blowing agents with an atmospheric pressure boiling point of at least 20° C. (68° F.). In certain embodiments, the blowing agent composition comprises a hydrocarbon with an atmospheric pressure boiling point of at least 20° C. (68° F.) and water. As used herein, "hydrocarbon" refers to chemical compounds composed primarily of carbon and hydrogen that may contain heteroatoms such as oxygen, nitrogen, sulfur, or other elements. In certain embodiments, halogenated blowing agents with a global warming potential ("GWP")≥25 (100 year) and ozone depletion potential ("ODP")>0 are not used in the practice of the present invention.

Specific examples of suitable hydrocarbons with an atmospheric pressure boiling point of at least 20° C. (68° F.) include, but are not limited to, n-pentane (atmospheric pressure boiling point of 36.1° C. (96.9° F.)), isopentane (atmospheric pressure boiling point of 27.7° C. (81.9° F.)), cyclopentane (atmospheric pressure boiling point of 49° C. (120.2° F.)), hexane (atmospheric pressure boiling point of 68° C. (154.4° F.)), 2,2-dimethylbutane (atmospheric pressure boiling point of 50° C. (122° F.)), 2-methylpentane (atmospheric pressure boiling point of 60° C. (140° F.)), 1-hexene (atmospheric pressure boiling point of 63° C. (145.4° F.)), 1-pentene (atmospheric pressure boiling point of 30° C. (86° F.)), acetone (atmospheric pressure boiling point of 56° C. (132.8° F.)), acetaldehyde (atmospheric pressure boiling point of 20.2° C. (68.4° F.)), dimethyl carbonate (atmospheric pressure boiling point of 90° C. (194° F.)), methylal (atmospheric pressure boiling point of 42.3° C. (108.1° F.)), ethyl formate (atmospheric pressure boiling point of 54.3° C. (129.7° F.)), methyl acetate (atmospheric pressure boiling point of 56.9° C. (134.4° F.)), and methyl formate (atmospheric pressure boiling point of 31.8° C. (89.2° F.)). As will of course be appreciated, mixtures of two or more of any of the foregoing or unlisted suitable hydrocarbons can be used. In certain embodiments, the hydrocarbons with an atmospheric pressure boiling point of at least 20° C. (68° F.) is n-pentane, isopentane, cyclopentane, methyl formate, and/or methylal.

In certain embodiments, the hydrocarbon with an atmospheric pressure boiling point of at least 20° C. (68° F.) is present in an amount of at least 1% by weight, such as at least 2% by weight, or, in some cases, at least 3% by weight and up to 10% by weight, such as up to 8% by weight, or, in some cases, up to 6% by weight, based on total weight of the foam-forming composition.

In addition to the hydrocarbon blowing agent, some water is often included in the blowing agent composition. As will be appreciated, water reacts with isocyanates to produce carbon dioxide gas as an auxiliary blowing agent. The amount of water included in the foam-forming composition will often range from 0.05% to 1.0% by weight, such as 0.1% to 0.8% by weight, based on total weight of the foam-forming composition.

If desired, it is also possible that the blowing agent composition comprises a hydrocarbon, such as a hydrofluoroolefin, having an atmospheric pressure boiling point of less than 20° C. (68° F.), specific examples of which include, but are not limited to, butane (atmospheric pressure boiling point of −1° C. (30.2° F.)), isobutane (atmospheric pressure boiling point of −11.7° C. (10.9° F.)), butylene (atmospheric pressure boiling point of −6.6° C. (20.1° F.)), isobutylene (atmospheric pressure boiling point of −6.9° C. (19.6° F.)), trans-1-chloro-3,3,3-trifluoropropene (atmospheric pressure boiling point of 19° C. (66.2° F.)), and dimethyl ether (atmospheric pressure boiling point of −24° C. (−11.2° F.)).

In addition, the first polyisocyanurate foam-forming composition may include any of a variety of optional ingredients.

The first polyisocyanurate foam-forming composition also often includes a flame retardant composition. Suitable flame retardants for use in the foam-forming composition include, without limitation, halogenated, such as brominated flame retardants, such as brominated polyols, and phosphonated flame retardants, such as a halogenated, such as chlorinated, phosphates.

In certain embodiments, the brominated flame retardant comprises a brominated polyether polyol of the general formula (I):

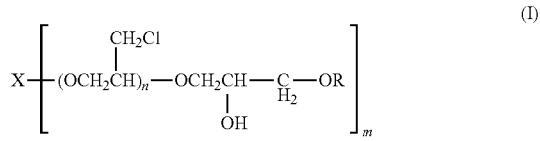

in which n is a number of 0 to 7, m is a number of 2 to 3; X is a saturated or unsaturated brominated polyol residue; and R is hydrogen or an alkyl group having 1 to 5 carbon atoms. Specific examples of suitable brominated polyether polyols are commercially available as Ixol® B-251 and Ixol® M-125 from Solvay Fluorides LLC, which are believed to be produced using the procedure described U.S. Pat. Nos. 4,020,024, 4,067,911 and 4,072,638. Other suitable brominated flame retardants include, but are not limited to, 3,4,5,6-tetrabromophthalic acid, tribromoneopentyl alcohol, 1,3-propanediol, 2,2-bis(bromomethyl), and pentabromophenyl ether, among others, including mixtures of two or more thereof. Suitable commercially available brominated flame retardants also include those available from ICL Industrial Products as the SaFRon® (6000 Series) brominated flame retardants. Mixtures of two or more of such brominated flame retardants can be used. In certain embodiments, the brominated flame retardant does not contain phosphorous.

Specific examples of suitable phosphorous compounds, such as halogenated phosphates, include, without limitation, tris-(2-chloroethyl)phosphate, tris-(2-chloroisopropyl)phosphate (TCPP), tris(1,3-dichloroisopropyl)phosphate, tris-(2,3-dibromopropyl)phosphate and tetrakis-(2-chloroethyl) ethylene diphosphate, Diethyl Bis-(2-hydroxyethyl)-aminomethylphosphonate, phosphoric acid, triethyl ester, polymer with oxirane and phosphorus oxide ($P_2O_5$), triethyl phosphate, including mixtures of two or more thereof. Isocyanate-reactive and/or non-reactive non-halogenated phosphorous compounds are often used.

In certain embodiments, the total amount of flame retardant in the first polyisocyanurate foam-forming composition is at least 1% by weight, such as at least 2% by weight and no more than 10% by weight, such as no more than 5% by weight, based on the total weight of the foam-forming composition.

In certain embodiments, the first polyisocyanurate foam-forming composition comprises a surfactant to, for example, stabilize the foaming reaction mixture until it obtains rigidity. Such surfactants often comprise a liquid or solid organosilicon compound, a polyethylene glycol ether of a long chain alcohol, a tertiary amine, an alkanolamine salt of a long chain alkyl acid sulfate ester, an alkylsulfonic ester, or an alkylarylsulfonic acid, or a mixture thereof. Such surfactants are employed in amounts sufficient to stabilize the foaming reaction mixture against collapse and the formation of large and uneven cells. Often, 0.1 to 10% by weight of the surfactant is used, based on the total weight of the foam-forming composition.

In certain embodiments, one or more catalysts are used in the foam-forming composition. Any suitable catalyst may be used including tertiary amines, such as, without limitation, triethylenediamine, N-methylmorpholine, pentamethyl diethylenetriamine, dimethylcyclohexylamine, tetra-methylethylenediamine, 1-methyl-4-dimethylaminoethyl-piperazine, 3-methoxy-N-dimethyl-propylamine, N-ethylmorpholine, diethylethanol-amine, N-cocomorpholine, N,N-dimethyl-N',N'-dimethylisopropyl-propylene diamine, N,N-diethyl-3-diethyl aminopropylamine and dimethyl-benzyl amine. A catalyst for the trimerization of polyisocyanates, such as an alkali metal alkoxide or carboxylate, or certain tertiary amines, are often employed. Such catalysts are used in an amount which measurably increases the rate of reaction of the polyisocyanate. Typical amounts are 0.1 to 10.0% by weight, based on the total weight of the foam-forming composition.

In certain methods of the present invention, a first polyisocyanurate faced foam laminate is prepared from the first polyisocyanurate foam-forming composition. Such faced foamed laminates are produced by reacting the organic polyisocyanate and the isocyanate-reactive composition in the presence of the blowing agent composition. Any of the known techniques for producing a rigid polyisocyanurate faced foam laminate may be used. As used herein, the term "polyisocyanurate faced foam laminate" refers to a structure comprising a polyisocyanurate foam core having two major surfaces and a facing material adhered to at least one of the major surfaces of the foam. As indicated, in the present invention, the foam in such polyisocyanurate faced foam laminate is a rigid foam, which for purposes of the present invention refers to a foam that meets the compressive strength and flexural strength values listed in Table 1 of ASTM C1289-15.

Processes for producing polyisocyanurate faced foam laminates from foam-forming compositions are known to those skilled in the art. Examples of suitable processes include: methods for producing polyisocyanurate laminated boardstock insulation, froth-forming method for continuously producing glass fiber reinforced insulation boards in accordance with teachings of U.S. Pat. No. 4,572,865, continuous or discontinuous methods for producing insulated metal panels, and methods for producing molded or free-rise rigid foam articles. Another suitable method is disclosed in U.S. Pat. No. 8,106,106, which is also incorporated herein by reference.

In the polyisocyanurate faced foam laminate, the facing material adhered to at least one of the major surfaces of the foam often comprises a layer or layers of organic and/or inorganic fibers or flexible foils, such as aluminum foils. Suitable natural organic fibers include, but are not limited to, cotton and cotton waste fibers; regenerated cellulose staple fibers and cellulose acetate fibers. Suitable synthetic organic fibers include, but are not limited to, polyester fibers, polyamide fibers, polyvinyl acetal fibers, and polypropylene fibers. Suitable inorganic fibers include, but are not limited to, glass fibers, glass wool fibers, mineral wool fibers, rock wool fibers and slag wool fibers. Combinations of the above fibers also can be used. The fibrous layer(s) is typically such that a polymeric foam which is frothed in place on the layer(s) can be readily introduced among the fibers thereof without penetrating or wetting entirely through the layer(s). In certain embodiments, a fiber glass facer mat comprising chopped glass fibers oriented in a random pattern and bonded together with a suitable binder is used.

In certain embodiments, the first polyisocyanurate faced foam laminate is produced by a method comprising: (a) conveying a lower fibrous facing layer along a production line: (b) mixing an organic polyisocyanate and a isocyanate-reactive composition in the presence of the blowing agent composition to form a foaming mixture; (c) depositing the foaming mixture onto the lower fibrous facing layer as it is conveyed along the production line; and (d) allowing the foaming mixture to expand and contact an advancing upper fibrous facing layer as it is conveyed along the production line. Such methods are described, for example, in U.S. Pat. No. 4,572,865 at col. 4, line 58 to col. 9, line 47, the cited portion of which being incorporated herein by reference.

In certain embodiments, the resulting faced foam laminate has a core foam density of less than 1.80 lb/ft$^3$ (28.8 kg/m$^3$), such as 1.50 to 1.80 lb/ft$^3$ (24.0 to 28.8 kg/m$^3$). Moreover, in certain embodiments, the thickness of the fully expanded foam core is from 0.25 to 6 inches (6.35 to 152.4 millimeters), such as 1 to 4 inches (25.4 to 101.6 millimeters), or, in some cases, 1.5 to 3 inches (38.1 to 76.2 millimeters).

In accordance with the methods of the present invention, the LTTR of the first polyisocyanurate faced foam laminate foam prepared as described above is measured in accordance with CAN/UL S770-09 at a plurality of temperatures to identify a calculated inflection point temperature below which defines a first mathematical correlation between temperature and the LTTR of the first polyisocyanurate faced foam laminate and above which defines a second mathematical correlation between temperature and the LTTR of the first polyisocyanurate faced foam laminate. In certain embodiments, the LTTR of the first polyisocyanurate faced foam laminate is measured in accordance with CAN/UL S770-09 at (i) a plurality of temperatures, such as at least 3, at least 4, at least 5, at least 6, at least 7, or, in some cases, at least 8 temperatures less than 75° F. (23.9° C.), such as a plurality of temperatures within the range of 20° F. to less than 75° F. (−6.7° C. to less than 23.9° C.), and (ii) a plurality of temperatures at 75° F. (23.9° C.) and higher, such as at least 3 or at least 4 temperatures at and above 75° F. (23.9° C.), such as a plurality of temperatures within the range of 75° F. to 105° F. (23.9° C. to 40.6° C.) to identify a calculated inflection point temperature below which defines a first mathematical correlation between temperature and the LTTR of the first polyisocyanurate faced foam laminate and above which defines a second mathematical correlation between temperature and the LTTR of the first polyisocyanurate faced foam laminate. In the present invention, the plurality of insulation mean temperatures and the temperature differences between the parallel plates should be chosen such that the practices described in ASTM C1058 (2010), Standard Practice for Selecting Temperatures for Evaluating and Reporting Thermal Properties of Thermal Insulation, Section 4 and ASTM C1045 (2007), Standard Practice for Calculating Thermal Transmission Properties under Steady State Conditions, Section 6.2 are followed. In some embodiments of the present process, the LTTR of the first polyisocyanurate faced foam laminate is less than 5.4 ft$^2$·hr·° F./BTU·inch (0.936 m$^2$·° C./W@25 mm) at some temperatures within the temperature range of 10° F. to 75° F. (−12.2° C. to 23.9° C.). For example, in certain embodiments, the LTTR of the first polyisocyanurate faced foam laminate is less than 5.4 ft$^2$·hr·° F./BTU·inch (0.936 m$^2$·° C./W@25 mm) at temperatures with the range of 10° F. to 40° F. (−12.2° C. to 4.44° C.).

More particularly, for purposes of the present invention, the calculated inflection point temperature is the temperature at which a line having a negative slope as defined by a linear regression fit of the LTTR measurements within the temperature range where LTTR increases with decreasing temperature (hereinafter a "warm side line") intersects with a line having a positive slope as defined by a linear regression fit of the LTTR measurements within the temperature range where LTTR decreases with decreasing temperature (hereinafter a "cold side line"). These linear regressions fits define the mathematical correlations between temperature and LTTR for the first polyisocyanurate faced foam laminate. The Examples herein illustrate how to identify a calculated inflection point temperature of the first polyisocyanurate faced foam laminate and how to define mathematical correlations between temperature and the LTTR of the first polyisocyanurate faced foam laminate in accordance with the methods of the present invention.

In accordance with the methods of the present invention, the mathematical correlations defined as described above are used to identify a plurality of predicted mathematical correlations between temperature and the LTTR of the first polyisocyanurate faced foam laminate at a plurality of reduced inflection point temperatures below the calculated inflection point temperature.

In certain embodiments of the present invention, the plurality of predicted mathematical correlations between temperature and the LTTR of the first polyisocyanurate faced foam laminate at a plurality of reduced inflection point temperatures below the calculated inflection point temperature are determined by a process that comprises defining estimated cold side lines at a plurality of reduced inflection point temperatures. In certain embodiments, a selected reduced inflection point temperature is used to calculate LTTR ("calculated LTTR") using the warm side line defined by the linear regression fit of the measured LTTR's of the first polyisocyanurate faced foam laminate as described above, wherein such a line is defined by the Equation:

$$y_{calc} = (m_w \cdot x) + b_w,$$

in which $y_{calc}$ is LTTR in ft$^2$·hr·° F./BTU·inch; x is the selected reduced inflection point temperature in ° F., and $m_w$ and $b_w$ are values defined by the linear regression fit in which $m_w$ defines the slope of the warm side line of the linear regression fit and $b_w$ defines the LTTR axis ("y axis") intercept value of the warm side line of the linear regression fit.

In a next step, the foregoing calculated LTTR is used to determine a calculated y-intercept "b" of a calculated cold side line at the selected reduced inflection point temperature by using the following equation:

$$b_{c\text{-}calc} = y_{calc} - (m_c \cdot x)$$

in which $y_{calc}$ is the calculated LTTR in ft$^2$·hr·° F./BTU·inch; x is the selected reduced inflection point temperature in ° F.; $m_c$ is the slope of the cold side line of the linear regression fit described above; and $b_{c\text{-}calc}$ is the calculated y-intercept "b" of the estimated cold side line at the selected reduced inflection point temperature. Once $b_{c\text{-}calc}$ is known, an estimated cold side line at the selected reduced inflection point temperature is defined mathematically based on the values for $b_{c\text{-}calc}$ and $m_c$.

In accordance with certain embodiments of the present invention, the procedure described in the two immediately preceding paragraphs is repeated at a plurality of reduced inflection point temperatures to identify a plurality of estimated cold side lines for the first polyisocyanurate faced foam laminate at a plurality of reduced inflection point temperatures.

According to the methods of the present invention, the plurality of estimated mathematical correlations, i.e., estimated cold side lines, between temperature and LTTR of the first polyisocyanurate faced foam laminate at a plurality of reduced inflection point temperatures below the calculated inflection point temperature is used to design a second polyisocyanurate foam-forming composition that is different from the first polyisocyanurate foam-forming composition and which comprises a blowing agent composition comprising one or more hydrocarbon blowing agents with an atmospheric pressure boiling point of at least 68° F. (20° C.), wherein the second polyisocyanurate foam-forming composition produces a second polyisocyanurate faced foam laminate having a LTTR of at least 5.4 ft$^2$·hr·° F./BTU·inch (0.936 m$^2$·° C./W@25 mm) at all mean insulation temperatures within a temperature range of 10° F. to 75° F. (−12.2° C. to 23.9° C.), when measured according to CAN/UL S770-09.

In certain embodiments, to design such a second polyisocyanurate foam-forming composition according to the methods of the present invention, the plurality of estimated mathematical correlations, i.e., estimated cold side lines, between temperature and the LTTR of the first polyisocyanurate faced foam laminate at a plurality of temperatures below the calculated inflection point temperature are used to determine a predicted inflection point temperature range where heating energy consumption of a selected building type in geographic locations where HDD65 values are greater than 2000 that is insulated with a polyisocyanurate foam insulation would be equal to or lower than the heating energy consumption for the selected building type in the same geographic location that is insulated with a theoretical insulation having a selected constant LTTR of, for example, 5.77 ft$^2$·hr·° F./BTU·inch (1.00 m$^2$·° C./W@25 mm) at all temperatures within the range of 10° F. to 75° F. (−12.2° C. to 23.9° C.). This predicted inflection point temperature is then used to design a second polyisocyanurate foam-forming composition that is different from the first polyisocyanurate foam-forming composition and which comprises a blowing agent composition comprising one or more hydrocarbon blowing agents with an atmospheric pressure boiling point greater of at least 68° F. (20° C.), wherein the second polyisocyanurate foam-forming composition produces a second polyisocyanurate faced foam laminate having a LTTR of at least 5.4 ft$^2$·hr·° F./BTU·inch (0.936 m$^2$·° C./W@25 mm) at all mean insulation temperatures within a temperature range of 10° F. to 75° F. (−12.2° C. to 23.9° C.), when measured according to CAN/UL S770-09.

Further, in certain embodiments, the second polyisocyanurate faced foam laminate has a calculated heat-loss weighted R-value greater than 5.5 ft$^2$·hr·° F./BTU·inch (0.95 m$^2$·° C./W@25 mm) in locations where HDD65 values are greater than 2000, determined as described below. The value of HDD65 at a given location is calculated by means well-known to those skilled in the art, and is described in ASHRAE Handbook of Fundamentals at pp. 14.11 and 19.16 (2013), the cited portions of which being incorporated herein by reference.

In certain embodiments, to determine a predicted inflection point temperature range where heating energy consumption of a selected building type in geographic locations where HDD65 values are greater than 2000 that is insulated with a polyisocyanurate foam insulation would be equal to or lower than the heating energy consumption for the selected building type in the same geographic location that is insulated with a theoretical insulation having a selected constant LTTR of, for example, 5.77 ft$^2$·hr·° F./BTU·inch (1.00 m$^2$·° C./W@25 mm) at all temperatures within the range of 10° F. to 75° F. (−12.2° C. to 23.9° C.), a whole building energy simulation program, known as EnergyPlus (version 8.3.0), can be used, in which the Conduction Finite Difference (CFD) algorithm is selected for the desired surfaces across which heat transfer is to be examined. As those skilled in the art will appreciate, the EnergyPlus (version 8.3.0) CFD algorithm represents a wall, floor, or roof surface (as selected by the user) by discretizing the wall, floor, or roof into several nodes (Δx being the distance between nodes) using a fully implicit scheme for a homogeneous material with uniform node spacing. CFD uses a discretization method to establish Δx—the distance between nodes—which strives for a balance of precision and avoidance of computation overload.

The calculation method is according to equation (1):

$$C_p \rho \Delta x \{(T_i^{j+1} - T_i^j)/\Delta t\} = k_W \{(T_{i+1}^{j+1} - T_i^{j+1})/\Delta x\} + k_E \{(T_{i-1}^{j+1} - T_i^{j+1})/\Delta x\} \quad (1)$$

in which T is node temperature (in ° C., K); Δt is the calculation time step (hour); Δx is the finite difference layer thickness (meters); $k_w$ is the thermal conductivity for interface between i node and i+1 node (W/mK); $k_E$ is the thermal conductivity for interface between i node and i−1 node (W/mK); i is the node being modeled; i+1 is the adjacent node to the interior of the construction; i−1 is the adjacent node to the exterior of the construction; j+1 is the new time step; j is the previous time step; $C_p$ is specific heat (J/kg·K); and ρ is density (kg/m$^3$).

The CFD algorithm is iterative in that it continues to use improved guesses for both surface temperatures until it converges to a value within a tolerance range. EnergyPlus requires initial input allowing the program to determine a thermal conductivity associated with any value of node temperature. These inputs are (i) thermal conductivities (k) and temperatures from the plurality of estimated mathematical correlations described above, (ii) the thermal conductivity (k) value for a theoretical faced foam laminate in which thermal conductivity is assumed to be constant regardless of temperature, such as a thermal conductivity based on a constant R-value of 5.77 ft$^2$·hr·° F./BTU·inch (1.00 m$^2$·° C./W@25 mm), (iii) building type, such as a Department of Energy Prototype Strip Mall, and selected locations where HDD65 values are greater than 2000, such as at least 3, at least 4, at least 5, or, in some cases, at least 6 or at least 7 locations within Climate Zones 4-7, such as, for example, Baltimore, Md., Chicago, Ill., Vancouver, British Columbia, Toronto, Ontario, Burlington, Vt., Calgary, Alberta, and Duluth, Minn.

The EnergyPlus CFD algorithm is also described in Verification and Validation of EnergyPlus Conduction Finite Difference and Phase Change Material Models for Opaque Wall Assemblies, Tabares-Velasco et al., National Renewable Energy Laboratory Technical Report NREL/TP-5500-55792 (July 2012).

Based on the foregoing inputs, EnergyPlus uses a linear solution to execute whole building simulations to determine a thermal conductivity associated with any temperature between two sequential input value pairs and to estimate an annual building heating energy consumption for each inputted location. The output of EnergyPlus is an estimate of the annual heating energy consumption for the selected building type at each selected location. The estimates are compared to one another to identify the predicted inflection point temperature range where estimated building heating energy consumption is equal to or lower than the estimated building heating energy consumption for the selected building type in the same geographic location that is insulated with a theoretical insulation having a selected constant LTTR of, for example, 5.77 ft$^2$·hr·° F./BTU·inch (1.00 m$^2$·° C./W@25 mm) at all temperatures within the range of 10° F. to 75° F. (−12.2° C. to 23.9° C.). The Examples herein illustrate how to determine such a predicted inflection point temperature range in accordance with the present invention.

According to the methods of the present invention, this predicted inflection point temperature range is then used to design a second polyisocyanurate foam-forming composition that is different from the first polyisocyanurate foam-forming composition and which comprises a blowing agent composition comprising one or more hydrocarbon blowing agents with an atmospheric pressure boiling point of at least 68° F. (20° C.), wherein the second polyisocyanurate foam-forming composition produces a second polyisocyanurate faced foam laminate having a LTTR of at least 5.4 ft$^2$·hr·° F./BTU·inch (0.936 m$^2$·° C./W@25 mm), when measured according to CAN/UL S770-09. In certain embodiments, the second polyisocyanurate faced foam laminate has a calculated heat-loss weighted R-value greater than 5.5 ft$^2$·hr·° F./BTU·inch (0.95 m$^2$·° C./W@25 mm) in locations where HDD65 values are greater than 2000.

In particular, in certain methods of the present invention, the design of a second polyisocyanurate foam-forming composition comprises identifying a second hydrocarbon blowing agent composition that is different in composition from the hydrocarbon blowing agent of the first polyisocyanurate foam-forming composition. In certain embodiments, based on comparison of the estimated heating consumption difference relative to a building insulated with an insulation having a constant LTTR, such as 5.77 ft$^2$·hr·° F./BTU·inch (1.00 m$^2$·° C./W@25 mm) in a selected temperature range (such as 0° to 75° F. (−17.8° to 23.9° C.)), for a preselected target foam density (such as a density in the range of 1.50 to 1.80 lb/ft$^3$ (24.0 to 28.8 kg/m$^3$)), a second hydrocarbon blowing agent composition is identified that has a calculated condensation temperature within or less than the predicted inflection point temperature range where heating energy consumption of a selected building type in geographic locations where HDD65 values are greater than 2000 that is insulated with a polyisocyanurate foam insulation would be equal to or lower than the heating energy consumption for the selected building type in the same geographic location that is insulated with a theoretical insulation having a selected constant LTTR of, for example, 5.77 ft$^2$·hr·° F./BTU·inch (1.00 m$^2$·° C./W@25 mm) at all temperatures within the range of 10° F. to 75° F. (−12.2° C. to 23.9° C.).

In certain embodiments, to identify such a second blowing agent composition, a multi-step process is used in which, in a first step, a calculated mass of blowing agent needed to make a foam having the preselected target foam density is determined where condensation of the blowing agent does not occur above the targeted inflection point temperature. To do this, a derivative of the Clausius Clapyeron equation called the Antoine equation that uses an empirical three parameter fit to predict the saturated vapor pressure of a pure liquid at a given temperature is used. According to the Antoine equation:

$$\log P = A - B/(T+C)$$

wherein: (a) T is temperature in ° C.; (b) P is pressure in mmHg; (c) and A, B, and C are Antoine coefficients having values determined experimentally. The values for A, B, and C can be found in publically available reference sources. The Antoine coefficients for some exemplary hydrocarbon blowing agents are set forth in the Table below:

| Compound | A | B | C |
| --- | --- | --- | --- |
| n-pentane | 6.87632 | 1075.780 | 233.205 |
| Isopentane | 6.83315 | 1040.730 | 235.445 |
| Cyclopentane | 6.88676 | 1124.162 | 231.361 |
| Hexane | 6.87024 | 1168.720 | 224.210 |
| 2,2-dimethylbutane | 6.75483 | 1081.176 | 229.343 |
| 2-methylpentane | 6.83910 | 1135.410 | 226.572 |
| 1-hexene | 6.86572 | 1152.971 | 225.849 |
| 1-pentene | 6.84650 | 1044.895 | 233.516 |
| Acetone | 7.23160 | 1277.030 | 237.230 |
| Methyl Formate | 7.17040 | 1125.200 | 230.650 |
| Acetaldehyde | 7.05650 | 1070.600 | 236.010 |

As is apparent, the Antoine equation identifies the saturation vapor pressure of a pure liquid at a selected temperature.

In certain embodiments, by preselecting a target foam density, such as a density within the range of 1.50 to 1.8 lb/ft$^3$ (24.0 to 28.8 kg/m$^3$), the volume occupied by the solid polyurethane component of a selected amount of foam is subtracted (the density of a solid polyurethane component of a foam is assumed for purposes of the present invention to be 1245 g/L), to obtain the estimated volume of space that contains the blowing agent at the saturation vapor pressure of the blowing agent.

Next, in certain embodiments, the ideal gas law is used to calculate the maximum mass of a selected blowing agent that can be used to produce a foam having the preselected target foam density. According to the Ideal Gas law:

$$n = PV/RT,$$

wherein (i) n is moles of gas, (ii) P is the pressure of the gas in atmospheres, (iii) V is the volume of the gas in liters, R is the ideal gas constant (0.08206 L·atm/(mol·K)); and T is the temperature of the gas in Kelvin. Use of the Ideal Gas Law in which P is the predicted saturated vapor pressure as determined by the Antoine equation as described above and T is a selected calculated condensation temperature as described above, allows calculation of the maximum amount of particular blowing agent that can be used to avoid condensation of the blowing agent above the temperature T. In accordance with embodiments of the present invention, this process is repeated for any hydrocarbon blowing agent of interest for use in the formulation and a hydrocarbon blowing agent composition is selected in which the total mass of hydrocarbon blowing agent is selected according to the calculated mass of hydrocarbon blowing agent needed to make a foam having the preselected target foam density and the mass of each individual hydrocarbon blowing agent in the blowing agent composition is at or below the maximum amount of such blowing agent that can be used to avoid condensation of the blowing agent above the temperature T.

In accordance with certain embodiments of the methods of the present invention, a second polyisocyanurate foam-forming composition comprising the second blowing agent composition identified according to the procedure described above is prepared and a polyisocyanurate faced foam laminate from such a polyisocyanurate foam-forming composition is prepared. The second polyisocyanate foam-forming composition may include any of the components described above with respect to the first polyisocyanurate foam-forming composition provided that, as discussed earlier, the second polyisocyanarate foam-forming composition has a second hydrocarbon blowing agent composition that is different in composition from the blowing agent composition of the first polyisocyanurate foam-forming composition. The second polyisocyanurate foam-forming composition and the second polyisocyanurate faced foam laminate can be prepared as described earlier. In certain embodiments, the second polyisocyanurate faced foam laminate has a core foam density of less than 1.80 lb/ft$^3$ (28.8 kg/m$^3$), such as 1.50 to 1.80 lb/ft$^3$ (24.0 to 28.8 kg/m$^3$). Moreover, in certain embodiments, the thickness of the fully expanded foam core of the second polyisocyanurate faced foam laminate is from 0.25 to 6 inches (6.35 to 152.4 millimeters), such as 1 to 4 inches (25.4 to 101.6 millimeters), or, in some cases, 1.5 to 3 inches (38.1 to 76.2 millimeters).

Next, in certain embodiments, the long term thermal resistance value of such a polyisocyanurate faced foam laminate is measured in accordance with CAN/UL S770-09 at a plurality of temperatures, such as at least 3, at least 4, at least 5, at least 6, at least 7, or, in some cases, at least 8 temperatures less than 75° F. (23.9° C.), such as temperatures from 20° F. (−6.7° C.) to less than 75° F. (23.9° C.), and (ii) a plurality of temperatures at 75° F. (23.9° C.) and higher, such as at least 3 or at least 4 temperatures at and above 75° F. (23.9° C.), such as temperatures from 75° F. to 105° F. (23.9° C. to 40.6° C.). In fact, it was surprisingly discovered that, at least in certain cases, such measurements revealed that a single "cold side line" does not correctly reflect blowing agent composition condensation for a given second polyisocyanurate foam-forming composition and that the LTTR value for such a composition is at least 5.4 ft$^2$·hr·° F./BTU·inch (0.936 m$^2$·° C./W@25 mm) at all temperatures from 10° F. to 75° F. ((−12.2° C. to 23.9° C.). Without being bound by any theory, it is currently believed that a secondary inflection point within the temperature range from 10° F. to 75° F. ((−12.2° C. to 23.9° C.) occurs, in at least some cases, possibly due to condensation of water vapor in the cell gas mixture occurring within this temperature range.

In certain embodiments of the present invention, using the foregoing measurements, the EnergyPlus CFD algorithm is used again to conduct an energy performance assessment of the second polyisocyanurate faced foam laminate prepared from the second polyisocyanurate foam-forming composition to assess whether the designed second polyisocyanurate foam-forming composition has produced a second faced foam laminate having a calculated heat-loss weighted R-value greater than 5.5 ft$^2$·hr·° F./BTU·inch (0.955 m$^2$·° C./W@25 mm) in locations where HDD65 values are greater than 2000. In certain embodiments, this determination is done by selecting a particular building type and a plurality of locations within a range of climate zones. The Examples herein illustrate a suitable method for conducting this assessment and determining the calculated heat-loss weighted R-value of an insulation in accordance embodiments of the present invention.

As will be appreciated by the foregoing certain embodiments of the present invention are directed to methods for designing a polyisocyanurate foam-forming composition, comprising: (a) measuring the LTTR of a first polyisocyanurate faced foam laminate prepared from a first polyisocyanurate foam-forming composition comprising a blowing agent composition comprising one or more hydrocarbon blowing agents with an atmospheric pressure boiling point of at least 68° F. (20° C.), wherein the LTTR is measured according to CAN/UL S770-09 at a plurality of temperatures to identify a calculated inflection point temperature below which defines a first mathematical correlation between temperature and the LTTR of the first polyisocyanurate faced foam laminate and above which defines a second mathematical correlation between temperature and the LTTR of the first polyisocyanurate faced foam laminate; (b) identifying a plurality of predicted mathematical correlations between temperature and the LTTR of the first polyisocyanurate faced foam laminate at a plurality of reduced inflection point temperatures below the calculated inflection point temperature; and (c) using the plurality of predicted mathematical correlations to design a second polyisocyanurate foam-forming composition that is different from the first polyisocyanurate foam-forming composition and which comprises a blowing agent composition comprising one or more hydrocarbon blowing agents with an atmospheric pressure boiling point of at least 68° F. (20° C.), wherein the second polyisocyanurate foam-forming composition produces a second polyisocyanurate faced foam laminate that has a LTTR of at least 5.4 ft$^2$·hr·° F./BTU·inch (0.936 m$^2$·° C./W@25 mm) at all mean insulation temperatures within a temperature range of 10° F. to 75° F. (−12.2° C. to 23.9° C.), when measured according to CAN/UL S770-09.

In certain embodiments, the present invention is directed to a method of the previous paragraph, wherein the first polyisocyanurate foam-forming composition comprises: (a) an organic polyisocyanate (such as 4,4'-diphenylmethane diisocyanate (MDI), polymeric MDI (pMDI), toluene diisocyanate, allophanate-modified isocyanates, isocyanate-terminated prepolymers and carbodiimide-modified isocyanates, including pMDI having an average NCO functionality of from 2.2 to 3.3, such as 2.2 to 3.0 and a viscosity of from 25 to 2000 mPas, such as 25 to 800 mPas at 25° C. and prepolymers thereof prepared with polyols or other oligomers or polymers such as polyether or polyester polyols that contain active hydrogen atoms; (b) a polymeric polyol with a nominal functionality of at least 2.0 (such as a polyester polyol (such as an aromatic polyester polyol) and/or a polyether polyol, such as those having an average hydroxyl functionality of from 2 to 8, such as 2 to 6, or, in some cases, 2.0 to 2.5, and/or a hydroxyl number of 100 mg KOH/gm to 1000 mgKOH/gm or, in some cases, 200 mgKOH/gm to 500 mgKOH/gm, including, without limitation, blends of an aromatic polyester polyol and a polyester and/or polyether polyol that contains renewable content derived from incorporation of regenerable materials, such as fatty acid triglycerides, sugar, or natural glycerin, and (c) a blowing agent composition comprising one or more hydrocarbon blowing agents with an atmospheric pressure boiling point of at least 68° F. (20° C.), such as where the blowing agent composition comprises a hydrocarbon with an atmospheric pressure boiling point of at least 20° C. (68° F.) and water, such as where the hydrocarbon with an atmospheric pressure boiling point of at least 20° C. (68° F.) includes n-pentane, isopentane, cyclopentane, hexane, 2,2-dimethylbutane, 2-methylpentane, 1-hexene, 1-pentene, acetone, acetaldehyde, dimethyl carbonate, methylal, ethyl formate, methyl acetate, and/or methyl formate. In certain of these embodiments, halogenated blowing agents are not used in the practice of the present invention.

In some embodiments, the present invention is directed to a method of either of the previous two paragraphs, wherein the organic polyisocyanate(s) is/are included in the first foam-forming system, i.e., composition, in an amount of at least 50%, such as from 55% to 75%, or, in some cases, from 59% to 69% by weight, based on total weight of the foam-forming composition; and/or the polyol(s) is/are a present in an amount of 10% to 40%, such as 20% to 40%, or, in some cases, 25% to 35% by weight, based on total weight of the foam-forming composition; and/or the relative amounts of organic polyisocyanate and polymeric polyol(s) used in the first polyisocyanurate foam-forming composition are selected so as to provide the composition with a NCO:OH index of at least 1.8, such as at least 2.0, or, in some cases, 2.0 to 3.0; and/or the hydrocarbon with an atmospheric pressure boiling point of at least 20° C. (68° F.) is present in an amount of at least 1% by weight, such as at least 2% by weight, or, in some cases, at least 3% by weight and up to 10% by weight, such as up to 8% by weight, or, in some cases, up to 6% by weight, based on total weight of the foam-forming composition; and/or water is included in the first foam-forming composition in an amount ranging from 0.05% to 1.0% by weight, such as 0.1% to 0.8% by weight, based on total weight of the foam-forming composition.

Some embodiments of the present invention are directed to a method of any of the previous three paragraphs, wherein the blowing agent composition further comprises a hydrocarbon, such as a hydrofluoroolefin, having an atmospheric pressure boiling point of less than 20° C. (68° F.), such as butane, isobutane, butylene, isobutylene, trans-1-chloro-3,3,3-trifluoropropene, and/or dimethyl ether.

In some embodiments, the present invention is directed to a method of any of the previous four paragraphs, wherein the first polyisocyanurate foam-forming composition also includes a flame retardant composition comprising halogenated, such as brominated flame retardants, such as a brominated polyol, phosphonated flame retardants, such as a halogenated, such as chlorinated, phosphates, such as a brominated flame retardant comprising a brominated polyether polyol of the general formula (I):

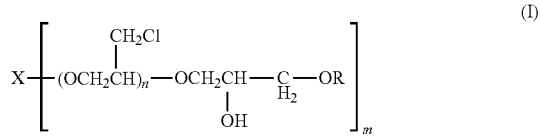

in which n is a number of 0 to 7, m is a number of 2 to 3; X is a saturated or unsaturated brominated polyol residue; and R is hydrogen or an alkyl group having 1 to 5 carbon atoms, and/or 3,4,5,6-tetrabromophthalic acid, tribromoneopentyl alcohol, 1,3-propanediol, 2,2-bis(bromomethyl), and/or pentabromophenyl ether. In some of these embodiments, the brominated flame retardant does not contain phosphorous. In some of these embodiments, the phosphorous compounds, such as halogenated phosphates, include, without limitation, tris-(2-chloroethyl)phosphate, tris-(2-chloroisopropyl)phosphate (TCPP), tris(1,3-dichloroisopropyl)phosphate, tris-(2,3-dibromopropyl)phosphate and tetrakis-(2-chloroethyl) ethylene diphosphate, Diethyl Bis-(2-hydroxyethyl)-aminomethylphosphonate, phosphoric acid, triethyl ester, polymer with oxirane and phosphorus oxide ($P_2O_5$), triethyl phosphate, including mixtures of two or more thereof. Isocyanate-reactive and/or non-reactive non-halogenated phosphorous compounds are often used in these embodiments.

In certain embodiments, the present invention is directed to a method of the previous paragraph, wherein the total amount of flame retardant in the first polyisocyanurate foam-forming composition is at least 1% by weight, such as at least 2% by weight and no more than 10% by weight, such as no more than 5% by weight, based on the total weight of the foam-forming composition.

Some embodiments of the present invention are directed to a method of any of the previous five paragraphs, wherein the first polyisocyanurate faced foam laminate is produced by a method comprising: (a) conveying a lower fibrous facing layer along a production line: (b) mixing an organic polyisocyanate and a isocyanate-reactive composition in the presence of the blowing agent composition to form a foaming mixture; (c) depositing the foaming mixture onto the lower fibrous facing layer as it is conveyed along the production line; and (d) allowing the foaming mixture to expand and contact an advancing upper fibrous facing layer as it is conveyed along the production line.

In some embodiments, the present invention is directed to a method of any of the previous six paragraphs wherein the first polyisocyanurate faced foam laminate has a core foam density of less than 1.80 lb/ft$^3$ (28.8 kg/m$^3$), such as 1.50 to 1.80 lb/ft$^3$ (24.0 to 28.8 kg/m$^3$) and/or the thickness of the fully expanded foam core is from 0.25 to 6 inches (6.35 to 152.4 millimeters), such as 1 to 4 inches (25.4 to 101.6 millimeters), or, in some cases, 1.5 to 3 inches (38.1 to 76.2 millimeters).

Certain embodiments of the present invention are directed to a method of any of the previous seven paragraphs, wherein the LTTR of the first polyisocyanurate faced foam laminate is measured in accordance with CAN/UL S770-09 at (i) at least 3, at least 4, at least 5, at least 6, at least 7, or, in some cases, at least 8 temperatures less than 75° F. (23.9° C.), such as a plurality of temperatures within the range of 20° F. to less than 75° F. (−6.7° C. to less than 23.9° C.), and/or (ii) at least 3 or at least 4 temperatures at and above 75° F. (23.9° C.), such as a plurality of temperatures within the range of 75° F. to 105° F. (23.9° C. to 40.6° C.) to identify a calculated inflection point temperature below which defines a first mathematical correlation between temperature and the LTTR of the first polyisocyanurate faced foam laminate and above which defines a second mathematical correlation between temperature and the LTTR of the first polyisocyanurate faced foam laminate.

Some embodiments of the present invention are directed to a method of any of the previous eight paragraphs, wherein the plurality of predicted mathematical correlations between temperature and the LTTR of the first polyisocyanurate faced foam laminate at a plurality of reduced inflection point temperatures below the calculated inflection point temperature are determined by a process that comprises defining estimated cold side lines at a plurality of reduced inflection point temperatures, such as by (i) using a selected reduced inflection point temperature to calculate LTTR using the warm side line defined by the linear regression fit of the measured LTTR's of the first polyisocyanurate faced foam laminate, wherein such a line is defined by the Equation:

$$y_{calc} = (m_w \cdot x) + b_w,$$

in which $y_{calc}$ is LTTR in ft²·hr·° F./BTU·inch; x is the selected reduced inflection point temperature in ° F., and $m_w$ and $b_w$ are values defined by the linear regression fit in which $m_w$ defines the slope of the warm side line of the linear regression fit and $b_w$ defines the LTTR axis ("y axis") intercept value of the warm side line of the linear regression fit; and (ii) using the calculated LTTR is used to determine a calculated y-intercept "b" of a calculated cold side line at the selected reduced inflection point temperature by using the equation:

$$b_{c\text{-}calc} = y_{calc} - (m_c \cdot x)$$

in which $y_{calc}$ is the calculated LTTR in ft²·hr·° F./BTU·inch; x is the selected reduced inflection point temperature in ° F.; $m_c$ is the slope of the cold side line of the linear regression fit described above; and $b_{c\text{-}calc}$ is the calculated y-intercept "b" of the estimated cold side line at the selected reduced inflection point temperature. In some of these embodiments, (i) and (ii) are repeated at a plurality of reduced inflection point temperatures to identify a plurality of estimated cold side lines for the first polyisocyanurate faced foam laminate at a plurality of reduced inflection point temperatures.

In certain embodiments, the present invention is directed to a method of any of the previous nine paragraphs, wherein, to design the second polyisocyanurate foam-forming composition, the plurality of estimated mathematical correlations between temperature and the LTTR of the first polyisocyanurate faced foam laminate at a plurality of temperatures below the calculated inflection point temperature are used to determine a predicted inflection point temperature range where heating energy consumption of a selected building type in geographic locations where HDD65 values are greater than 2000 that is insulated with a polyisocyanurate foam insulation would be equal to or lower than the heating energy consumption for the selected building type in the same geographic location that is insulated with a theoretical insulation having a selected constant LTTR of, for example, 5.77 ft²·hr·° F./BTU·inch (1.00 m²·° C./W@25 mm) at all temperatures within the range of 10° F. to 75° F. (−12.2° C. to 23.9° C.). In certain of these embodiments, to determine a predicted inflection point temperature range where heating energy consumption of a selected building type in geographic locations where HDD65 values are greater than 2000 that is insulated with a polyisocyanurate foam insulation would be equal to or lower than the heating energy consumption for the selected building type in the same geographic location that is insulated with a theoretical insulation having a selected constant LTTR of, for example, 5.77 ft²·hr·° F./BTU·inch (1.00 m²·° C./W@25 mm) at all temperatures within the range of 10° F. to 75° F. (−12.2° C. to 23.9° C.), a whole building energy simulation program in which a conduction finite difference algorithm is used to examine heat transfer across surfaces.

Some embodiments of the present invention are directed to a method of the previous paragraph, wherein the step of determining a predicted inflection point temperature range where heating energy consumption of a selected building type in geographic locations where HDD65 values are greater than 2000 that is insulated with a polyisocyanurate foam insulation would be equal to or lower than the heating energy consumption for the selected building type in the same geographic location that is insulated with a theoretical insulation having a selected constant LTTR at all temperatures within the range of 10° F. to 75° F. (−12.2° C. to 23.9° C.), comprises using a whole building energy simulation program in which a conduction finite difference algorithm is used to examine heat transfer across surfaces. In some of these embodiments, the predicted inflection point temperature range is 30° F. (−1.1° C.) to 40° F. (4.4° C.).

In some embodiments, the present invention is directed to a method of any of the previous eleven paragraphs, wherein the step of designing of the second polyisocyanurate foam-forming composition comprises: (1) determining a mass of blowing agent needed to make a foam of a selected mass and having a preselected target foam density using the Antoine equation; (2) determining the total volume occupied by the solid component of the selected mass of foam and subtracting this amount from the total volume to obtain an estimated volume of space that contains the blowing agent at the saturation vapor pressure of the blowing agent; (3) calculating the maximum mass of a selected blowing agent that can be used to produce a foam having the preselected target inflection point temperature using the Ideal Gas law; (4) repeating steps (1)-(3) for any hydrocarbon blowing agent of interest for use in the second polyisocyanurate foam-forming composition; and (5) selecting a hydrocarbon blowing agent composition in which the total mass of hydrocarbon blowing agent is at or below the maximum amount of such blowing agent that can be used to avoid condensation of the blowing agent above the target inflection point temperature.

Certain embodiments of the present invention are directed to a method of any of the previous twelve paragraphs, further comprising preparing the second polyisocyanurate foam-forming composition comprising the second blowing agent composition and preparing a second polyisocyanurate faced foam laminate from such a second polyisocyanurate foam-forming composition. Some of these methods further comprise measuring the LTTR of the second polyisocyanurate face foam laminate in accordance with CAN/UL S770-09 at (i) at least 3 temperatures less in the range of 20° F. (−6.7° C.) to less than 75° F. (23.9° C.), and (ii) at least 3 temperatures in the range of 75° F. to 105° F. (23.9° C. to 40.6° C.) and/or assessing whether the second faced foam laminate has a calculated heat-loss weighted R-value greater than 5.5 ft 2·hr·° F./BTU·inch in locations where HDD65 values are greater than 2000.

As will also be appreciated from the foregoing, some embodiments of the present invention are directed to methods for designing a polyisocyanurate foam-forming composition, comprising: (a) measuring the LTTR of a first polyisocyanurate faced foam laminate prepared from a first polyisocyanurate foam-forming composition comprising a blowing agent composition comprising one or more hydrocarbon blowing agents with an atmospheric pressure boiling point of at least 68° F., wherein the LTTR is measured according to CAN/UL S770-09 at a plurality of temperatures to identify a calculated inflection point temperature below which defines a first mathematical correlation between temperature and the LTTR of the first polyisocyanurate faced foam laminate and above which defines a second mathematical correlation between temperature and the LTTR of the first polyisocyanurate faced foam laminate; (b) identifying a plurality of predicted mathematical correlations between temperature and the LTTR of the first polyisocyanurate faced foam laminate at a plurality of reduced inflection point temperatures below the calculated inflection point temperature; (c) using the plurality of predicted mathematical correlations to determine a predicted inflection point temperature where energy consumption of a selected building type insulated with a polyisocyanurate foam insulation would be equal to or lower than the energy consumption for the selected building type when insulated with a theoretical insulation having a constant LTTR of 5.77 ft 2·hr·° F./BTU·inch at all temperatures within the range of 10° F. to 75° F.; and (d) using the predicted inflection point temperature to design a second polyisocyanurate foam-forming composition that is different from the first polyisocyanurate foam-forming composition and which comprises a blowing agent composition comprising one or more hydrocarbon blowing agents with an atmospheric pressure boiling point greater than or equal to 20° C., wherein the second polyisocyanurate foam-forming composition produces a second polyisocyanurate faced foam laminate that has a LTTR of at least 5.4 ft 2·hr·° F./BTU·inch at all mean insulation temperatures within a temperature range of 10° F. to 75° F., when measured according to CAN/UL S770-09.

In certain embodiments, the present invention is directed to the method of the immediately preceding paragraph, further comprising: (e) preparing the second polyisocyanurate foam-forming composition comprising the second blowing agent composition; and (f) preparing the second polyisocyanurate faced foam laminate from the second polyisocyanurate foam-forming composition, wherein the second polyisocyanurate faced foam laminate has a calculated heat-loss weighted R-value greater than 5.5 ft 2·hr·° F./BTU·inch in locations where HDD65 values are greater than 2000.

In yet other aspects, some embodiments of the present invention are directed to a polyisocyanurate faced foam laminate comprising a rigid foam that is the reaction product of a polyisocyanurate foam-forming composition comprising a blowing agent composition comprising one or more hydrocarbon blowing agents with an atmospheric pressure boiling point greater than or equal to 20° C., wherein the blowing agent composition is selected to provide a polyisocyanurate face rigid foam laminate having a LTTR of at least 5.4 ft 2·hr·° F./BTU·inch (0.936 m2·° C./W@25 mm) at all mean insulation temperatures within a temperature range of 10° F. to 75° F. (−12.2° C. to 23.9° C.), when measured according to CAN/UL S770-09.

In certain embodiments, the present invention is directed to a laminate of the immediately preceding paragraph, wherein the polyisocyanurate foam-forming composition comprises: (a) an organic polyisocyanate (such as 4,4'-diphenylmethane diisocyanate (MDI), polymeric MDI (pMDI), toluene diisocyanate, allophanate-modified isocyanates, isocyanate-terminated prepolymers and carbodiimide-modified isocyanates, including pMDI having an average NCO functionality of from 2.2 to 3.3, such as 2.2 to 3.0 and a viscosity of from 25 to 2000 mPas, such as 25 to 800 mPas at 25° C. and prepolymers thereof prepared with polyols or other oligomers or polymers such as polyether or polyester polyols that contain active hydrogen atoms; (b) a polymeric polyol with a nominal functionality of at least 2.0 (such as a polyester polyol (such as an aromatic polyester polyol) and/or a polyether polyol, such as those having an average hydroxyl functionality of from 2 to 8, such as 2 to 6, or, in some cases, 2.0 to 2.5, and/or a hydroxyl number of 100 mg KOH/gm to 1000 mgKOH/gm or, in some cases, 200 mgKOH/gm to 500 mgKOH/gm, including, without limitation, blends of an aromatic polyester polyol and a polyester and/or polyether polyol that contains renewable content derived from incorporation of regenerable materials, such as fatty acid triglycerides, sugar, or natural glycerin, and (c) a blowing agent composition comprising one or more hydrocarbon blowing agents with an atmospheric pressure boiling point of at least 68° F. (20° C.), such as where the blowing agent composition comprises a hydrocarbon with an atmospheric pressure boiling point of at least 20° C. (68° F.) and water, such as where the hydrocarbon with an atmospheric pressure boiling point of at least 20° C. (68° F.) includes n-pentane, isopentane, cyclopentane, hexane, 2,2-dimethylbutane, 2-methylpentane, 1-hexene, 1-pentene, acetone, acetaldehyde, dimethyl carbonate, methylal, ethyl formate, methyl acetate, and/or methyl formate. In certain of these embodiments, halogenated blowing agents are not used in the practice of the present invention.

In some embodiments, the present invention is directed to a laminate of either of the immediately preceding two paragraphs, wherein the organic polyisocyanate(s) is/are included in the foam-forming system, i.e., composition, in an amount of at least 50%, such as from 55% to 75%, or, in some cases, from 59% to 69% by weight, based on total weight of the foam-forming composition; and/or the polyol(s) is/are a present in an amount of 10% to 40%, such as 20% to 40%, or, in some cases, 25% to 35% by weight, based on total weight of the foam-forming composition; and/or the relative amounts of organic polyisocyanate and polymeric polyol(s) used in the polyisocyanurate foam-forming composition are selected so as to provide the composition with a NCO:OH index of at least 1.8, such as at least 2.0, or, in some cases, 2.0 to 3.0; and/or the hydrocarbon with an atmospheric pressure boiling point of at least 20° C. (68° F.) is present in an amount of at least 1% by weight, such as at least 2% by weight, or, in some cases, at least 3% by weight and up to 10% by weight, such as up to 8% by weight, or, in some cases, up to 6% by weight, based on total weight of the foam-forming composition; and/or water is included in the first foam-forming composition in an amount ranging from 0.05% to 1.0% by weight, such as 0.1% to 0.8% by weight, based on total weight of the foam-forming composition.

Some embodiments of the present invention are directed to a laminate of any of the immediately preceding three paragraphs, wherein the blowing agent composition further comprises a hydrocarbon, such as a hydrofluoroolefin, having an atmospheric pressure boiling point of less than 20° C. (68° F.), such as butane, isobutane, butylene, isobutylene, trans-l-chloro-3,3,3-trifluoropropene, and/or dimethyl ether.

In some embodiments, the present invention is directed to a laminate of any of the immediately preceding four paragraphs, wherein the polyisocyanurate foam-forming composition also includes a flame retardant composition comprising halogenated, such as brominated flame retardants, such as a brominated polyol, phosphonated flame retardants, such as a halogenated, such as chlorinated, phosphates, such as a brominated flame retardant comprising a brominated polyether polyol of the general formula (I):

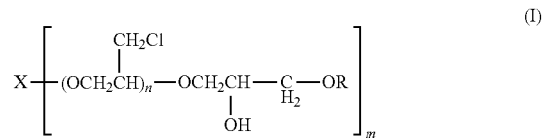

in which n is a number of 0 to 7, m is a number of 2 to 3; X is a saturated or unsaturated brominated polyol residue; and R is hydrogen or an alkyl group having 1 to 5 carbon atoms, and/or 3,4,5,6-tetrabromophthalic acid, tribromoneopentyl alcohol, 1,3-propanediol, 2,2-bis(bromomethyl), and/or pentabromophenyl ether. In some of these embodiments, the brominated flame retardant does not contain phosphorous. In some of these embodiments, the phosphorous compounds, such as halogenated phosphates, include, without limitation, tris-(2-chloroethyl)phosphate, tris-(2-chloroisopropyl)phosphate (TCPP), tris(1,3-dichloroisopropyl)phosphate, tris-(2,3-dibromopropyl)phosphate and tetrakis-(2-chloroethyl) ethylene diphosphate, Diethyl Bis-(2-hydroxyethyl)-aminomethylphosphonate, phosphoric acid, triethyl ester, polymer with oxirane and phosphorus oxide ($P_2O_5$), triethyl phosphate, including mixtures of two or more thereof. Isocyanate-reactive and/or non-reactive non-halogenated phosphorous compounds are often used in these embodiments.

In certain embodiments, the present invention is directed to a laminate of the immediately preceding paragraph, wherein the total amount of flame retardant in the first polyisocyanurate foam-forming composition is at least 1% by weight, such as at least 2% by weight and no more than 10% by weight, such as no more than 5% by weight, based on the total weight of the foam-forming composition.

Some embodiments of the present invention are directed to a laminate of any of the immediately preceding five paragraphs, wherein the first polyisocyanurate faced foam laminate is produced by a method comprising: (a) conveying a lower fibrous facing layer along a production line: (b) mixing an organic polyisocyanate and a isocyanate-reactive composition in the presence of the blowing agent composition to form a foaming mixture; (c) depositing the foaming mixture onto the lower fibrous facing layer as it is conveyed along the production line; and (d) allowing the foaming mixture to expand and contact an advancing upper fibrous facing layer as it is conveyed along the production line.

In some embodiments, the present invention is directed to a laminate of any of the immediately preceding six paragraphs wherein the first polyisocyanurate faced foam laminate has a core foam density of less than 1.80 lb/ft³ (28.8 kg/m³), such as 1.50 to 1.80 lb/ft³ (24.0 to 28.8 kg/m³) and/or the thickness of the fully expanded foam core is from 0.25 to 6 inches (6.35 to 152.4 millimeters), such as 1 to 4 inches (25.4 to 101.6 millimeters), or, in some cases, 1.5 to 3 inches (38.1 to 76.2 millimeters).

The non-limiting and non-exhaustive examples that follow are intended to further describe various non-limiting and non-exhaustive embodiments without restricting the scope of the embodiments described in this specification.

EXAMPLES

Example 1: Preparation of a First Polyisocyanurate Foam-Forming Composition

A polyisocyanurate foam-forming composition was prepared using the components and amounts (in parts by weight) listed in Table 1. The NCO and POLYOL were used in relative amount to provide an isocyanate index (ratio of the equivalent amount of isocyanate used relative to the theoretical equivalent of one equivalent isocyanate per one equivalent of hydroxyl) of 2.64.

TABLE 1

| Component | Amount |
|---|---|
| POLYOL[1] | 31.53 |
| Fyrol ® PCF[2] | 3.15 |
| Surfactant[3] | 0.47 |
| Dabco ® K-15[4] | 1.89 |
| Polycat ® 46[5] | 0.24 |
| PMDETA[6] | 0.085 |
| Water | 0.10 |
| n-Pentane | 5.64 |
| NCO[7] | 56.88 |

[1]Stepanpol ® PS-2352 polyester polyol having a functionality of 2 and an OH Value of 235 which is commercially available from the Stepan Company.
[2]an alkyl phosphate flame retardant based on Tris(2-chloroisopropyl) phosphate commercially available from ICL-Supresta
[3]Tegostab B8513, which is commercially available from Evonik Industries.
[4]Potassium octoate commercially available from Air Products Company.
[5]Potassium acetate commercially available from Air Products Company.
[6]Pentamethyldiethylenetriamine catalyst commercially available from Air Products Company.
[7]Polymeric MDI which is commercially available under the name Mondur ® 489 from Covestro LLC.

Example 2: Preparation of a First Polyisocyanurate Faced Foam Laminate

Polyisocyanurate laminated boardstock foam samples were prepared on a pilot-scale Hennecke unit at the Covestro LLC, Pittsburgh, Pa. facility in which the laminator is approximately 26 feet (7.92 meters) long and equipped with a single mix-head which makes boards that are 30 inches (0.76 meters) wide. The mix-head is outfitted with a two-stream "T" made with chlorinated polyvinyl chloride piping. The B side resin blend (i.e., isocyanate-reactive component) is premixed with the third-streamed blowing agent inline at 1800 psi (12.41 MPa) to 2500 psi (17.24 MPa) via a special Triple Action Dispersion Device (TADD) from Komax, Inc. prior to entering the static mixer and exiting the mix-head after being subjected to impingement mixing at 1800 psi (12.41 MPa) to 2500 psi (17.24 MPa). The conditions used for foams made in this study were as follows: Total Feed Rate—25 to 35 lbs/min (11.3 to 15.9 kg/min); Resin Temperature—82° F. (27.8° C.); Isocyanate Temperature—82° F. (27.8° C.); Platen Temperature—145° F. (62.8° C.); and Line Speed—25 to 38 ft/min (7.62 to 11.58 m/min).

The nominal board thicknesses for tested foam-forming composition of Table 1 was set at 2 inches (51 mm) and the foam was laminated with fiberglass reinforced cellulosic facer. The board was perforated on the top surface using a weighted spiked roller and on the bottom surface using a fixed spike roller as it exited the unit. The finished faced foam laminate was cut into 8' (2.44 m) long boards as it exited the laminator and the boards were stacked in bundles to cure as the chemical reaction went to completion.

The foam met standard foam physical properties requirements for Type II products in accordance with ASTM C 1289, Standard Specification for Faced Rigid Cellular Polyisocyanurate Thermal Insulation Board. Additional physical properties are listed in Table 2.

TABLE 2

| Property | Result |
| --- | --- |
| Core Density | 1.67 lb/ft³ (26.8 kg/m³) |
| Thickness | 2.21 inches (56.13 millimeters) |

Example 3: Measurement of Long Term Thermal Resistance and Determination of Calculated Inflection Point Temperature Ten of the boards produced as described in Example 2 were taken from the center of the foam bundle within 48 hours of production after cooling and three 2'×2' (0.61 m×0.61 m) samples were cut from each board and sealed, three samples per package. Two packages were unsealed each day over a successive five day period and used to prepare core and surface slices for thermal conductivity measurements at a different temperature on each day in accordance with a variable temperature modification of the CAN/UL S770-09 protocol.

The process was repeated so that another set of temperature measurements could be conducted to obtain a total of ten initial R-values at ten different temperatures. Results are set forth in Table 3.

TABLE 3

| Temperature | Initial R-value |
| --- | --- |
| 105° F. (40.6° C.) | 5.79 ft² · hr · ° F./Btu · inch (1.004 m² · ° C./W@25 mm) |
| 95° F. (35.0° C.) | 5.87 ft² · hr · ° F./Btu · inch (1.017 m² · ° C./W@25 mm) |
| 85° F. (29.4° C.) | 6.19 ft² · hr · ° F./Btu · inch (1.073 m² · ° C./W@25 mm) |
| 75° F. (23.9° C.) | 6.45 ft² · hr · ° F./Btu · inch (1.118 m² · ° C./W@25 mm) |
| 65° F. (18.3° C.) | 6.68 ft² · hr · ° F./Btu · inch (1.158 m² · ° C./W@25 mm) |
| 60° F. (15.6° C.) | 6.74 ft² · hr · ° F./Btu · inch (1.168 m² · ° C./W@25 mm) |
| 50° F. (10.0° C.) | 6.33 ft² · hr · ° F./Btu · inch (1.097 m² · ° C./W@25 mm) |
| 40° F. (4.4° C.) | 6.04 ft² · hr · ° F./Btu · inch (1.047 m² · ° C./W@25 mm) |
| 30° F. (−1.1° C.) | 5.74 ft² · hr · ° F./Btu · inch (0.995 m² · ° C./W@25 mm) |
| 20° F. (−6.7° C.) | 5.51 ft² · hr · ° F./Btu · inch (0.955 m² · ° C./W@25 mm) |

The core and surface slices were aged approximately 30 days to obtain the calculated LTTR values at ten different temperatures of a theoretical 3.2" (81 mm) thick faced foam laminate made with the foam-forming composition of Example 1. The results are set forth in Table 3a.

TABLE 3a

| Temperature | LTTR value |
| --- | --- |
| 105° F. (40.6° C.) | 5.19 ft² · hr · ° F./Btu · inch (0.900 m² · ° C./W@25 mm) |
| 95° F. (35.0° C.) | 5.24 ft² · hr · ° F./Btu · inch (0.908 m² · ° C./W@25 mm) |
| 85° F. (29.4° C.) | 5.56 ft² · hr · ° F./Btu · inch (0.964 m² · ° C./W@25 mm) |
| 75° F. (23.9° C.) | 5.90 ft² · hr · ° F./Btu · inch (1.023 m² · ° C./W@25 mm) |
| 65° F. (18.3° C.) | 5.97 ft² · hr · ° F./Btu · inch (1.035 m² · ° C./W@25 mm) |
| 60° F. (15.6° C.) | 5.97 ft² · hr · ° F./Btu · inch (1.035 m² · ° C./W@25 mm) |
| 50° F. (10.0° C.) | 5.56 ft² · hr · ° F./Btu · inch (0.964 m² · ° C./W@25 mm) |
| 40° F. (4.4° C.) | 5.27 ft² · hr · ° F./Btu · inch (0.913 m² · ° C./W@25 mm) |
| 30° F. (−1.1° C.) | 4.85 ft² · hr · ° F./Btu · inch (0.841 m² · ° C./W@25 mm) |
| 20° F. (−6.7° C.) | 4.50 ft² · hr · ° F./Btu · inch (0.780 m² · ° C./W@25 mm) |

The graphical representation of the two lines described by the data of Table 3 is in FIG. 1 along with the mathematical equations determined by a linear fit of the data. The intersection of the two lines at approximately 63° F. (17.2° C.) was the calculated inflection point temperature below which defined a first mathematical correlation between temperature and the long term thermal resistance value of the polyisocyanurate faced foam laminate (the cold side line) and above which defined a second mathematical correlation between temperature and the long term thermal resistance value of the polyisocyanurate faced foam laminate (the warm side line). In this case, the LTTR value of the faced foam laminate of Example 2 fell below 5.4 ft²·hr·° F./BTU·inch (0.936 m²·° C./W@25 mm) at about 44° F. (6.7° C.) based on solving for x in the equation for the line with the positive slope:

$$5.4 = 0.0365x + 3.77$$

Example 4: Identification of Estimated Mathematical Correlations Between Temperature and LTTR at Reduced Inflection Point Temperatures The mathematical correlations identified in Example 3 were used to identify a plurality of estimated mathematical correlations between temperature and the LTTR value of the polyisocyanurate faced foam laminate at a plurality of temperatures below the calculated inflection point temperature.

Mathematical calculations were done to generate new equations defining new lines with a positive slope (cold side line) that intersect with the existing line with a negative slope of Example 3 (warm side line). For example, to calculate the equation of the cold-side line where the onset of condensation occurs at 50° F. (10° C.), the LTTR value for the warm side vapor line at that temperature was determined by solving for y in the warm side equation identified in Example 3:

$$y_{calc} = -0.0222*50 + 7.46 \text{ where } y_{calc} = 6.35$$

Then, the y-intercept $b_{c-calc}$ of the equation for the new cold side line with the same slope as the cold side line identified in Example 3, but which intersects the warm side line at 50° F. (10° C.) where the LTTR value equals 6.35 ft²·hr·° F./Btu·inch (1.101 m²·° C./W@25 mm), was determined as follows: $6.35 = 0.0365*50 + b_{c-calc}$, $b_{c-calc} = 4.52$ Based on the foregoing, the equation for the new cold side liquid line where condensation begins at 50° F. was:
y=0.0365x+4.52

Figure 2:
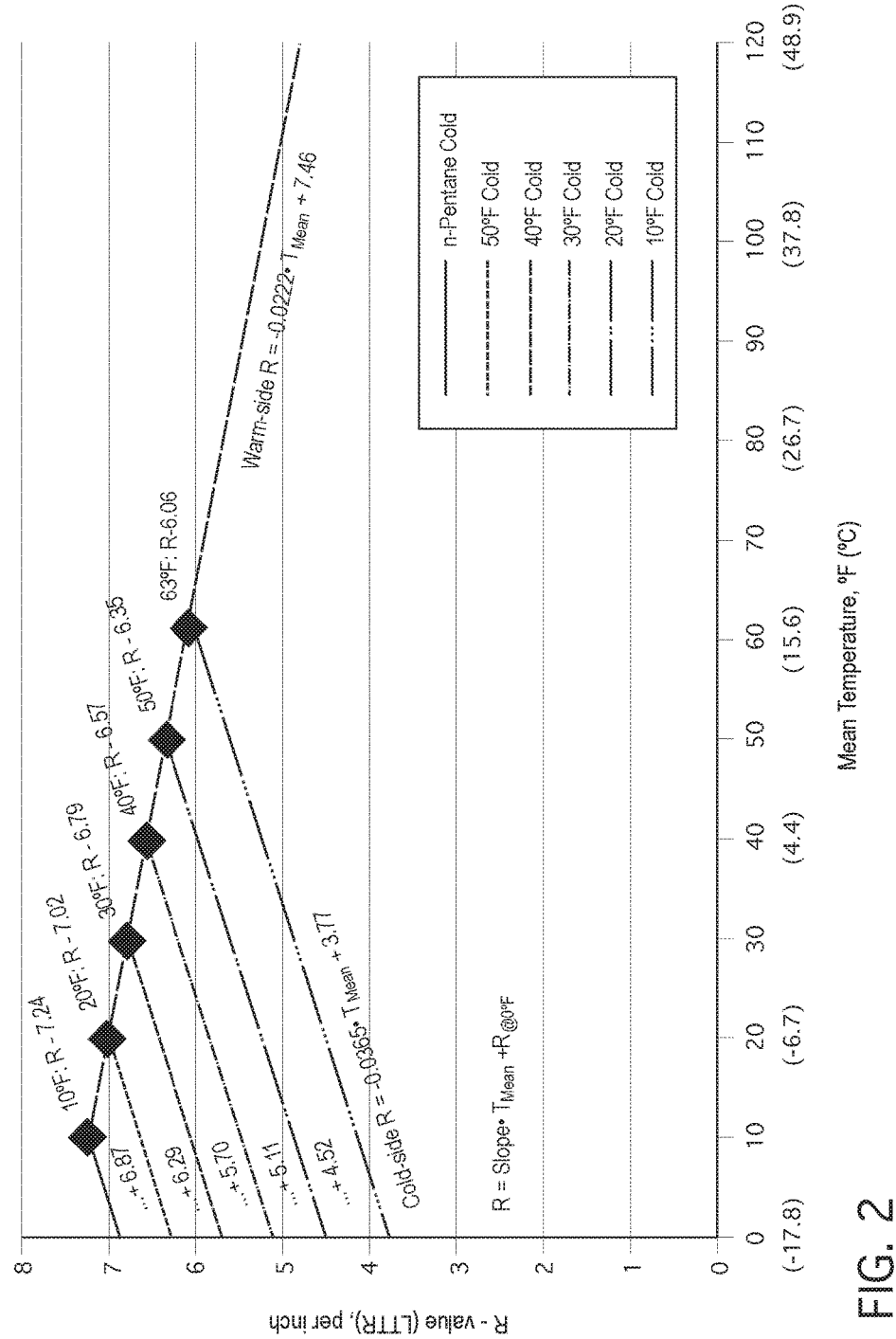
FIG. 2 is a graphical representation of the results of Example 4 in which a plurality of estimated mathematical correlations between temperature and the LTTR value of the polyisocyanurate faced foam laminate of Example 2 at a plurality of temperatures below the calculated inflection point temperature was identified.

The foregoing process was repeated to obtain the desired number of lines to provide LTTR values at different temperatures for use as one of the input variables or thermal performance profiles in modeling software to quantify changes in building energy consumption relative to a chosen LTTR value standard or baseline. Results are illustrated in FIG. 2 (TPE xx° F. refers to the selected reduced inflection point temperature and Generic n-Pentane refers to the insulation of Example 2) and data is set forth in Table 4A.

TABLE 4A

| Inflection Point Temperature | Property | R-value (ft² · hr · ° F./ Btu · inch) | Thermal Conductivity (Btu · inch/ ft² · hr · ° F.) | Thermal Conductivity (W/m² · ° C.) |
|---|---|---|---|---|
| 50° F. (10° C.) | Conductivity @ −45.56° C. (−50° F.) | 2.70 | 0.3711 | 0.05352 |
| | Conductivity @ 10° C. (50° F.) | 6.35 | 0.1576 | 0.02273 |
| | Conductivity @ 20° C. (68° F.) | 5.95 | 0.1681 | 0.02424 |
| | Conductivity @ 82.22° C. (180°) | 3.46 | 0.2887 | 0.04164 |
| 40° F. (4.4° C.) | Conductivity @ −45.56° C. (−50° F.) | 3.29 | 0.3044 | 0.04390 |
| | Conductivity @ 4.444° C. (40° F.) | 6.57 | 0.1522 | 0.02195 |
| | Conductivity @ 20° C. (68° F.) | 5.95 | 0.1681 | 0.02424 |
| | Conductivity @ 82.22° C. (180°) | 3.46 | 0.2887 | 0.04164 |
| 30° F. (1.1° C.) | Conductivity @ −45.56° C. (−50° F.) | 3.87 | 0.2581 | 0.03722 |
| | Conductivity @ −1.111° C. (30° F.) | 6.80 | 0.1472 | 0.02123 |
| | Conductivity @ 20° C. (68° F.) | 5.95 | 0.1681 | 0.02424 |
| | Conductivity @ 82.22° C. (180°) | 3.46 | 0.2887 | 0.04164 |
| 20° F. (−6.7° C.) | Conductivity @ −45.56° C. (−50° F.) | 4.46 | 0.2240 | 0.03230 |
| | Conductivity @ −6.667° C. (20° F.) | 7.02 | 0.1425 | 0.02055 |
| | Conductivity @ 20° C. (68° F.) | 5.95 | 0.1681 | 0.02424 |
| | Conductivity @ 82.22° C. (180°) | 3.46 | 0.2887 | 0.04164 |
| 10° F. (−12.2° C.) | Conductivity @ −45.56° C. (−50° F.) | 5.04 | 0.1982 | 0.02859 |
| | Conductivity @ −12.22° C. (10° F.) | 7.24 | 0.1382 | 0.01993 |
| | Conductivity @ 20° C. (68° F.) | 5.95 | 0.1681 | 0.02424 |
| | Conductivity @ 82.22° C. (180°) | 3.46 | 0.2887 | 0.04164 |
| Product of Example 2 | Conductivity @ −45.56° C. (−50° F.) | 1.94 | 0.5142 | 0.07417 |
| | Conductivity @ 17.14° C. (62.85° F.) | 6.06 | 0.1649 | 0.02378 |
| | Conductivity @ 20° C. (68° F.) | 5.95 | 0.1681 | 0.02424 |
| | Conductivity @ 82.22° C. (180°) | 3.46 | 0.2887 | 0.04164 |

Example 5: Identification of Predicted Inflection Point where Building Heating Energy Consumption is Equal to or Lower than the Energy Used for an Insulation Having a Selected Constant LTTR in Locations where HDD65 Values are Greater than 2000

EnergyPlus and the Commercial Prototype Building Model, Strip Mall were used to identify a predicted inflection point temperature range where building heating energy consumption would be equal to or lower than the energy used for an insulation having a constant LTTR of 5.77 ft²·hr·° F./Btu·inch (1.00 m²·° C./W@25 mm) in geographic locations where HDD65 values are greater than 2000.

The theoretically predicted thermal performance profiles identified in Example 4 at five (5) inflection point temperatures (10° F. (−12.2° C.), 20° F. (−6.7° C.), 30° F. (−1.1° C.), 40° F. (4.4° C.), and 50° F. (10° C.)) were used to provide input data for the EnergyPlus simulation tool utilizing the Conduction Finite Difference advance algorithm. Whole building simulations were executed on permutations of the five (5) profiles identified in Example 4, the profile identified in Example 3 for the face foam laminate of Example 2, and an insulation having a constant thermal conductivity ("Constant K") calculated from an LTTR of 5.77 ft²·hr·° F./Btu·inch (1.00 m²·° C./W@25 mm) The inputs are set forth in Table 5.

TABLE 5

| | Example 5A | Example 5B | Example 5C | Example 5D | Example 5E | Example 5F | Example 5G |
|---|---|---|---|---|---|---|---|
| Description | Constant K | Example 3 Profile | 50° F. (10° C.) Inflection Point | 40° F. (4.4° C.) Inflection Point | 30° F. (−1.1° C.) Inflection Point | 20° F. (−6.7° C.) Inflection Point | 10° F. (−12.2° C.) Inflection Point |
| Temperature (° C.) | −45.56 | −45.56 | −45.56 | −45.56 | −45.56 | −45.56 | −45.56 |
| Thermal Conductivity (W/m · K) | 0.02499 | 0.07414 | 0.05343 | 0.04388 | 0.03723 | 0.03233 | 0.02857 |
| Temperature (° C.) | 20 | 17.14 | 10 | 4.444 | −1.111 | −6.667 | −12.22 |
| Thermal Conductivity (W/m · K) | 0.02499 | 0.02378 | 0.02271 | 0.02194 | 0.02123 | 0.02056 | 0.01993 |
| Temperature (° C.) | 82.22 | 20 | 20 | 20 | 20 | 20 | 20 |
| Thermal Conductivity (W/m · K) | 0.02499 | 0.02424 | 0.02424 | 0.02424 | 0.02424 | 0.02424 | 0.02424 |
| Temperature (° C.) | | 82.22 | 82.22 | 82.22 | 82.22 | 82.22 | 82.22 |
| Thermal Conductivity (W/m · K) | | 0.04164 | 0.04164 | 0.04164 | 0.04164 | 0.04164 | 0.04164 |

Figure 3:
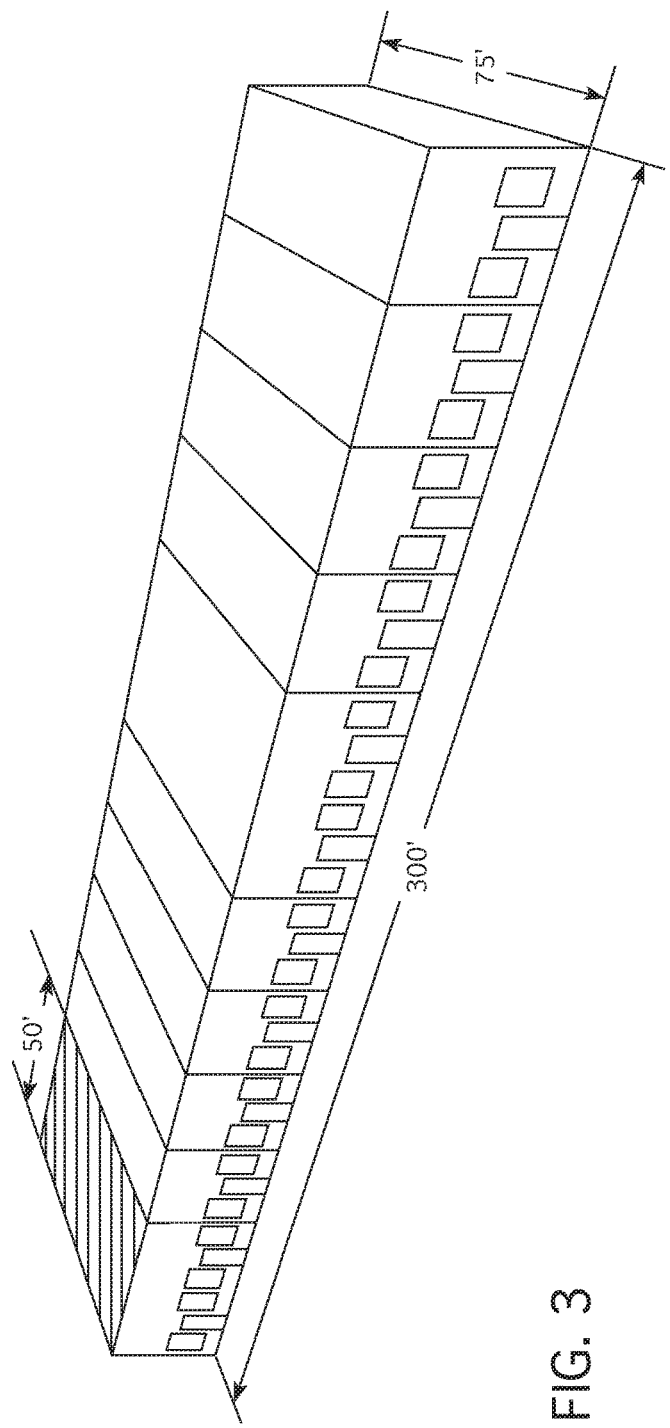
FIG. 3 is a depiction of a Department of Energy Prototype Strip Mall (having a building area of 2090.32 m$^2$) used for the EnergyPlus modeling conducted in Example 5.

EnergyPlus modeling was conducted on all scenarios for 7 locations spread through Climate Zones 4-7 using the Department of Energy Prototype Strip Mall (having a building area of 2090.32 m²) depicted in FIG. 3. Results are set forth in Table 6.

TABLE 6

| | Location | | | | | | |
|---|---|---|---|---|---|---|---|
| | Baltimore | Chicago | Vancouver | Toronto | Burlington | Calgary | Duluth |
| Climate Zone | 4A | 5A | 5C | 6A | 6A | 7 | 7 |
| Weather File WMO# | 724060 | 725300 | 718920 | 716240 | 726170 | 718770 | 727450 |
| Heating Energy, GJ (Fuel: natural gas) | | | | | | | |
| Example 5A | 318.7 | 534.1 | 369.6 | 681.1 | 654.0 | 682.6 | 866.4 |
| Example 5B | 333.2 | 555.1 | 381.1 | 705.9 | 678.2 | 716.5 | 899.0 |
| Example 5C | 320.3 | 536.3 | 366.7 | 683.0 | 656.5 | 688.1 | 871.7 |
| Example 5D | 315.1 | 528.4 | 362.5 | 674.3 | 649.0 | 677.2 | 860.7 |
| Example 5E | 312.9 | 524.7 | 361.1 | 670.2 | 644.7 | 671.3 | 855.0 |
| Example 5F | 312.0 | 523.3 | 360.7 | 668.1 | 642.8 | 668.9 | 852.3 |
| Example 5G | 312.0 | 523.0 | 360.9 | 667.6 | 642.1 | 668.2 | 851.4 |

Figure 4:
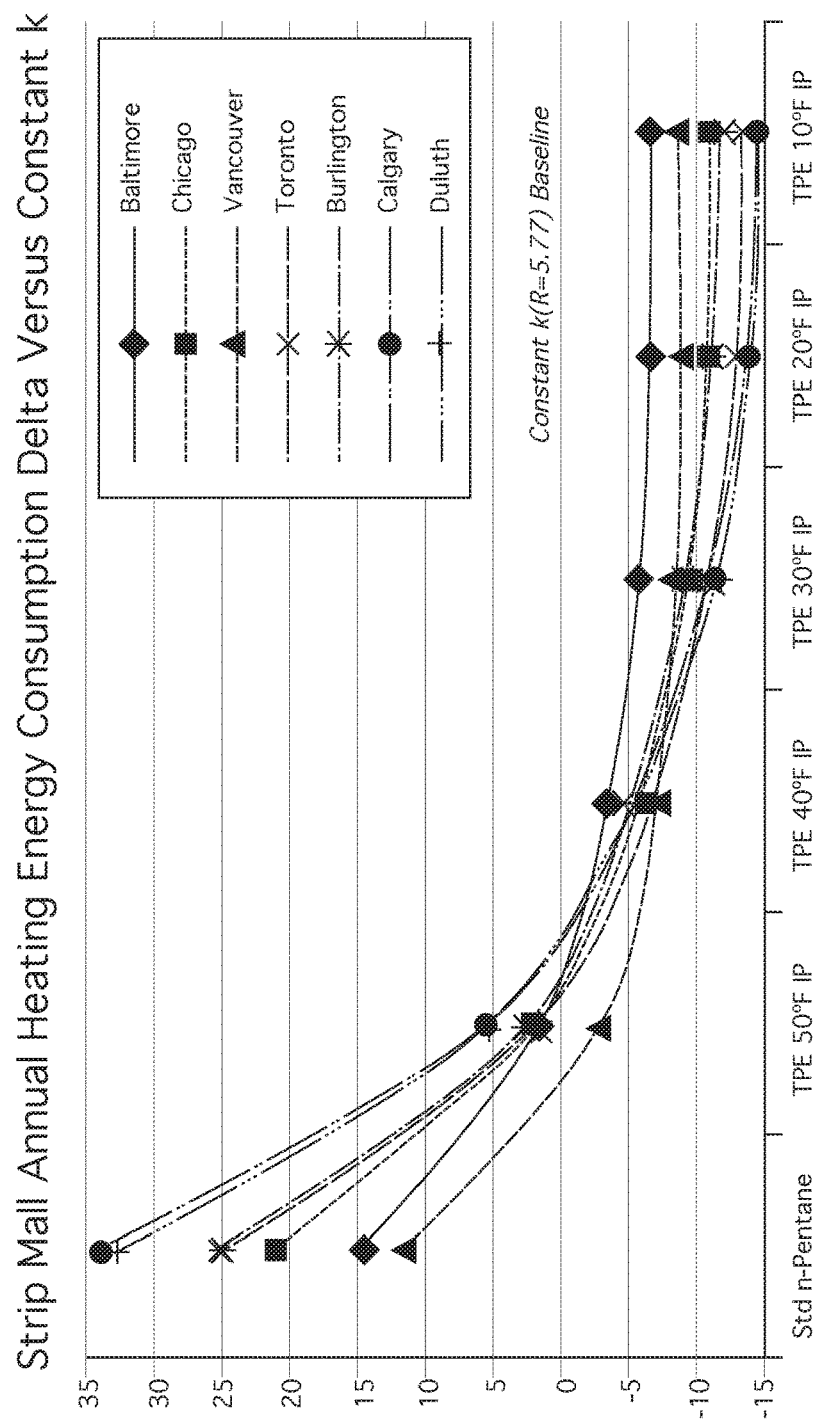
FIG. 4 illustrates the results compiled in Example 5 and illustrates the difference in heating energy consumption between Example 5A and Examples 5B-5G at various geographic locations.

The difference in heating energy consumption between Example 5A and Examples 5B-5G at each location were compiled. Results are set forth in Table 7 and illustrated in FIG. 4.

TABLE 7

| Example | Baltimore | Chicago | Vancouver | Toronto | Burlington | Calgary | Duluth |
|---|---|---|---|---|---|---|---|
| Example 5B | 14.5 | 21.0 | 11.5 | 24.8 | 24.3 | 33.9 | 32.6 |
| Example 5C | 1.6 | 2.2 | −2.9 | 1.8 | 2.5 | 5.5 | 5.3 |
| Example 5D | −3.6 | −5.7 | −7.1 | −6.8 | −4.9 | −5.4 | −5.7 |
| Example 5E | −5.8 | −9.4 | −8.6 | −11.0 | −9.3 | −11.2 | −11.4 |
| Example 5F | −6.7 | −10.8 | −9.0 | −13.0 | −11.1 | −13.7 | −14.1 |
| Example 5G | −6.8 | −11.1 | −8.8 | −13.5 | −11.8 | −14.4 | −15.0 |

Example 6: Design of a Polyisocyanurate Foam-Forming Composition

Based on the data produced in Example 5, a hydrocarbon blowing agent composition was identified in which condensation of the blowing agent composition would occur when the foam insulation average temperature is between 40° F. (4.4° C.) and 30° F. (−1.1° C.), since, based on the data of Example 5, such an inflection point temperature range should reduce heating energy consumption in all relevant climate zones. One liquid hydrocarbon blowing agent composition that would be expected to achieve this objective comprises isopentane and n-pentane. Since the boiling points of isopentane and n-pentane are 82° F. (27.8° C.) and 97° F. (36.1° C.) respectively, such a composition can be adjusted to contain a sufficient amount of the lower boiling component (isopentane) to lower the temperature where the onset on condensation will begin at a lower temperature relative to the composition of Example 1 but not so much that excessive frothing will occur as the foaming chemical mixture, at a typical temperature of 85° F. (29.4° C.) to 90° F. (32.2° C.), is applied to the fiberglass-reinforced facer. about 1.68 lb/ft³, the Antoine equation was used to determine the saturation vapor pressure of isopentane at 30° F. (−1.11° C.) and 40° F. (4.4° C.). According to this equation, the saturation vapor pressure of isopentane at 30° F. (−1.11° C.) is:

$$\log P = 6.833 - 1040.73/(-1.11 + 235.44), P = 246.43 \text{ mmHg}$$

Based on the Antoine equation, condensation of isopentane would begin to occur when its foam cell gas pressure is equal to or greater than 246.43 mmHg (4.9 psia). For an arbitrarily selected 200 grams of foam with a selected density of 1.68 lb/ft³ (26.91 gm/L), the volume of the foam was calculated to be 7.432 liters. The 200 grams of polyurethane was calculated to occupy a volume of 0.161 liters based on the simplification that all the foam mass is in the polyurethane solid with a density of 1245 gm/L. The polyurethane solids volume was subtracted from the foam total volume to result in a void space occupied by the gas of 7.271 liters where the cell gas pressure is equal to 246.43 mmHg (0.3242 atm). To solve for the number of moles of isopentane in the 200 grams of foam that accounts for 0.3242 atmospheres of cell gas pressure when the foam temperature is −1.11° C. (272.04 K), the ideal gas law was used:

$$n=(0.3242\times7.271)/(0.08206\times272.04)=0.1056 \text{ moles}$$

Since the molecular weight of isopentane is 72 gram/mole, no more than about 7.60 grams of isopentane blowing agent can be used in 200 grams of foam (or about 3.8% by weight, based on total weight of the foam) to achieve a foam having the selected density of 1.68 lb/ft³ (26.91 gm/L) for condensation to begin at 30° F. (−1.1° C.). Similarly, the saturation vapor pressure of isopentane at 40° F. (4.4° C.) is calculated to be 311.67 mmHg (0.4101 atm) according to the Antoine equation. Again, use of the Ideal Gas Law shows that no more than about 0.1308 moles of isopentane (4.71%) can be used in 200 grams of foam for condensation of the blowing agent to begin at about 40° F. (4.4° C.). These results are shown in Table 8 along with calculated maximum allowable values for n-pentane and cyclopentane that were obtained using the aforementioned process. Generally, about 0.1567 total moles of blowing agent (5.64%) in 200 grams of foam is needed to make the first polyisocyanurate faced foam laminate with a core foam density of 1.68 lb/ft³ (26.91 gm/L) using the pilot laminator unit of Example 2. The total amount of blowing agent needed to make the same density foam for another unit would vary depending upon the laminator type and configuration, chemical temperatures, catalyst levels, processing conditions, mix head type and configuration, and other parameters. It is apparent from Table 8 that the most suitable blend of blowing agents to make the second polyisocyanurate faced foam laminate at the targeted density would include isopentane as the primary blowing agent in combination with n-pentane since this mixture allows the highest total blowing agent concentration in the foam with a targeted core density of about 1.68 lb/ft³ where condensation of the blowing agent composition would not occur above the optimal foam insulation mean temperature inflection temperature range between 40° F. (4.4° C.) and 30° F. (−1.1° C.). Although a blend containing cyclopentane is also suitable due to its lower thermal conductivity, flexibility in achieving the targeted density would be limited since up to only 1.93% to 1.52% can be present in the foam whereas up to 3.37% to 2.69% n-pentane can be used. There is an implicit assumption in all of the above calculations that all blowing agents are in the gas phase as long as no condensation is occurring and that all components of the blend behave as ideal gases. So, the isopentane component of a 70/30 blend of isopentane/n-pentane at 5.62% in the foam will start to condense while the n-pentane component will remain in the gas phase. The n-pentane blowing agent (1.69% by weight, based on total weight of the foam) in the 70/30 isopentane/n-pentane blend has a cell gas pressure of 0.1470 atmospheres, well below its saturated vapor pressure at 30° F. (−1.1° C.) of 0.2291 atmospheres.

TABLE 8

| Blowing Agent (Thermal Conductivity Btu/ft · hr · ° F.) | Temperature ° F. (° C.) | BA Vapor Pressure (atmospheres) | BA Calculated Cell Gas Pressure (atmospheres) | % BA in foam gas phase | Condensation |
|---|---|---|---|---|---|
| Isopentane | 30 (−1.11) | 0.3242 | 0.3242 | 3.80 | Yes |
| (0.00825 | 40 (4.40) | 0.4101 | 0.3419 | 3.93 | No |
| @77° F.) | | | 0.4101 | 4.71 | Yes |
| n-Pentane | 30 (−1.11) | 0.2291 | 0.1470 | 1.69 | No |
| (0.00866 | | | 0.2291 | 2.69 | Yes |
| @77° F.) | 40 (4.40) | 0.2934 | 0.2934 | 3.37 | Yes |
| Cyclopentane | 30 (−1.11) | 0.1330 | 0.1330 | 1.52 | Yes |
| (0.00742 | 40 (4.40) | 0.1730 | 0.1730 | 1.93 | Yes |
| @77° F.) | | | | | |

As is apparent, according to these calculations, the amount of n-pentane in the foam would have to be equal to or greater than 2.69% before n-pentane condensation would begin to occur. So, a 58.6/41.4 blend of isopentane/n-pentane would exhibit simultaneous condensation of both blowing agents if the mixture comprised 6.49% of the foam mass assuming ideal gas behavior.

Example 7: Preparation of the Second Polyisocyanurate Foam-Forming Composition and Polyisocyanurate Faced Foam Laminate A polyisocyanuarate foam-forming composition was prepared using the components and amounts (in parts by weight) listed in Table 9 in which a blowing agent composition comprised 70% by weight isopentane and 30% by weight n-pentane, based on the total weight of the hydrocarbon blowing agent in the composition, for the purpose of making a foam where the onset of condensation would be expected to occur between 30° F. (−1.11° C.) and 40° F. (4.4° C.) based on Table 8. The NCO and POLYOL where used in relative amount to provide an isocyanate index (ratio of the equivalent amount of isocyanate used relative to the theoretical equivalent of one equivalent isocyanate per one equivalent of hydroxyl) of 2.64.

TABLE 9

| Component | Amount |
|---|---|
| POLYOL[1] | 31.42 |
| Fyrol ® PCF[2] | 3.14 |
| Surfactant[3] | 0.79 |
| Dabco ® K-15[4] | 1.89 |
| Polycat ® 46[5] | 0.24 |
| PMDETA[6] | 0.085 |
| Water | 0.10 |
| n-Pentane | 1.69 |
| Isopentane | 3.94 |
| NCO[7] | 61.67 |

[1]Stepanpol ® PS-2352 polyester polyol having a functionality of 2 and an OH Value of 235 which is commercially available from the Stepan Company.
[2]an alkyl phosphate flame retardant based onTris(2-chloroisopropyl) phosphate commercially available from ICL-Supresta
[3]Tegostab B8513, which is commercially available from Evonik Industries.
[4]Potassium octoate commercially available from Air Products Company.
[5]Potassium acetate commercially available from Air Products Company.
[6]Pentamethyldiethylenetriamine catalyst commercially available from Air Products Company.
[7]Polymeric MDI which is commercially available under the name Mondur ® 489 from Covestro LLC.

A polyisocyanurate faced foam laminate based on this composition was prepared using the equipment and procedure described in Example 2 and LTTR measurements were conducted in accordance with S770-09 using the procedure of Example 3 to define mathematical correlations that provide LTTR values at different temperatures.

The foam met standard foam physical properties requirements for Type II products in accordance with ASTM C 1289, Standard Specification for Faced Rigid Cellular Polyisocyanurate Thermal Insulation Board. Additional physical properties are listed in Table 10.

TABLE 10

| Property | Result |
| --- | --- |
| Core Density | 1.62 lb/ft³ (25.9 kg/m³) |
| Thickness | 2.51 inches (63.75 millimeters) |

It was surprisingly observed that a single cold side liquid line did not describe liquid condensation for this formulation. Inflection points observed in the foam at about 48° F. (8.89° C.) and about 30° F. (−1.11° C.) with the higher temperature value presumed to correspond to the onset of condensation of water vapor in the cell gas. The laboratory environment in which the foam slices were conditioned was kept at 70° F. (21.11° C.) and at about 50% relative humidity in accordance with CAN/UL S770-09. If a similar relative humidity existed in the cell gas, then the dew point for water condensation would be about 50.5° F. (10.28° C.) and that process would offset the normal improvement in LTTR at lower temperatures until all water vapor in the cell had condensed, which occurred at about 35° F. (1.67° C.). Below that temperature, the LTTR values correspond to the "true" cold side line for isopentane condensation in the second polyisocyanurate faced foam laminate. The inflection point for the intersection of the "true" cold side line and the warm side line for 5.62% 70/30 isopentane/n-pentane blend in the foam is 38.9° F. (3.85° C.) based on the linear regressions for the two lines. All LTTR values for the second polyisocyanurate faced foam laminate were greater than 5.4 ft²·hr·° F./Btu·inch (0.936 m²·° C./W@25 mm) in the temperature range of 20° F. (−6.7° C.) to 75° F. (23.9° C.) despite onset of condensation occurring at about 48° F. (8.9° C.), as is illustrated in FIG. 5.

Example 8: Calculation of Heat Loss Weighted R-Value

Figure 5:
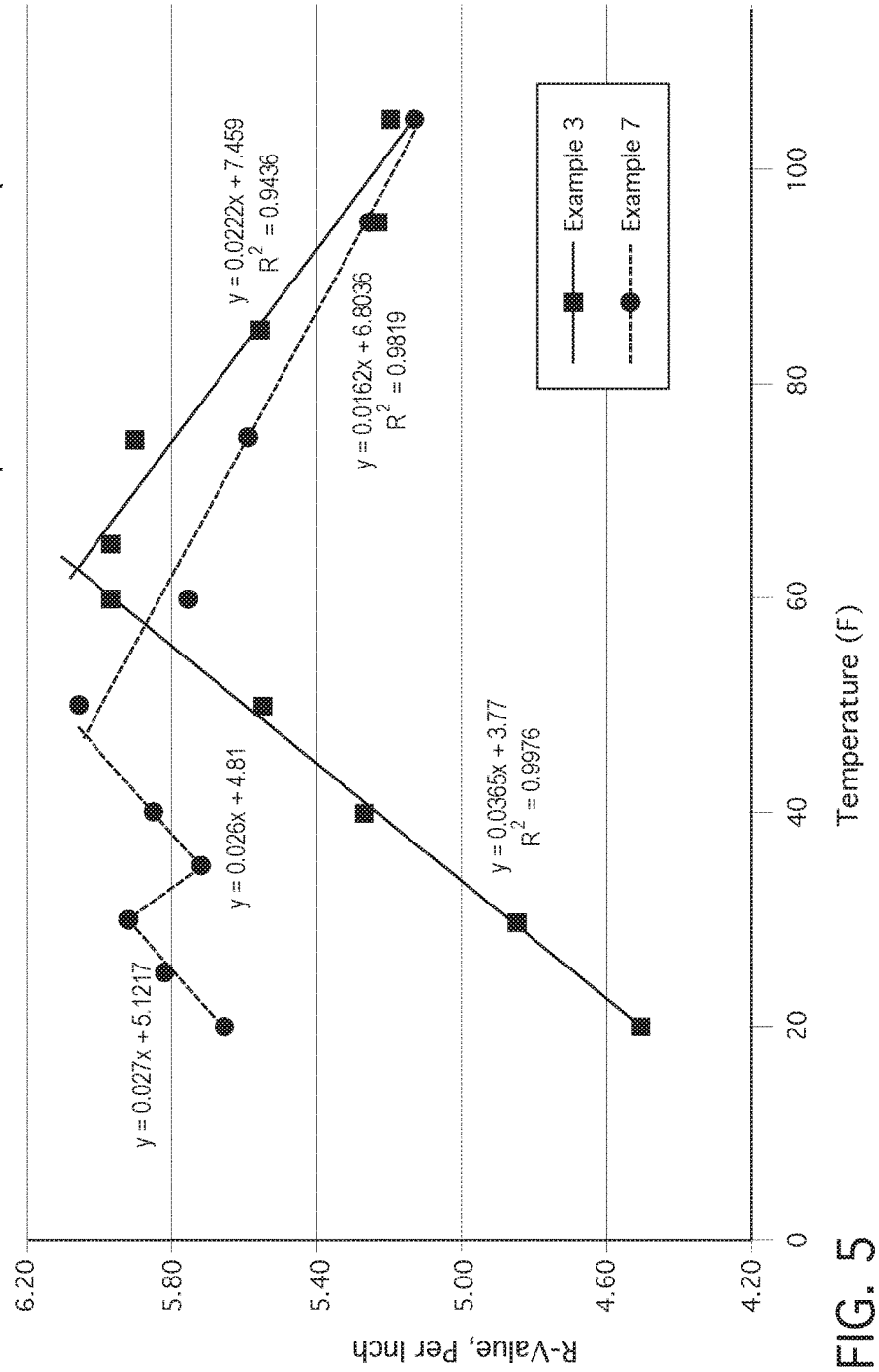
FIG. 5 is a graphical representation of the LTTR measurements conducted in Example 7, which includes mathematical equations determined by a linear fit of the data.

The mathematical correlations defining the lines illustrated in FIG. 5 for describing the temperature dependent LTTR behavior of the insulation produced in Example 7 were used calculate the heat loss weighted R-value of the insulation.

Figure 6:
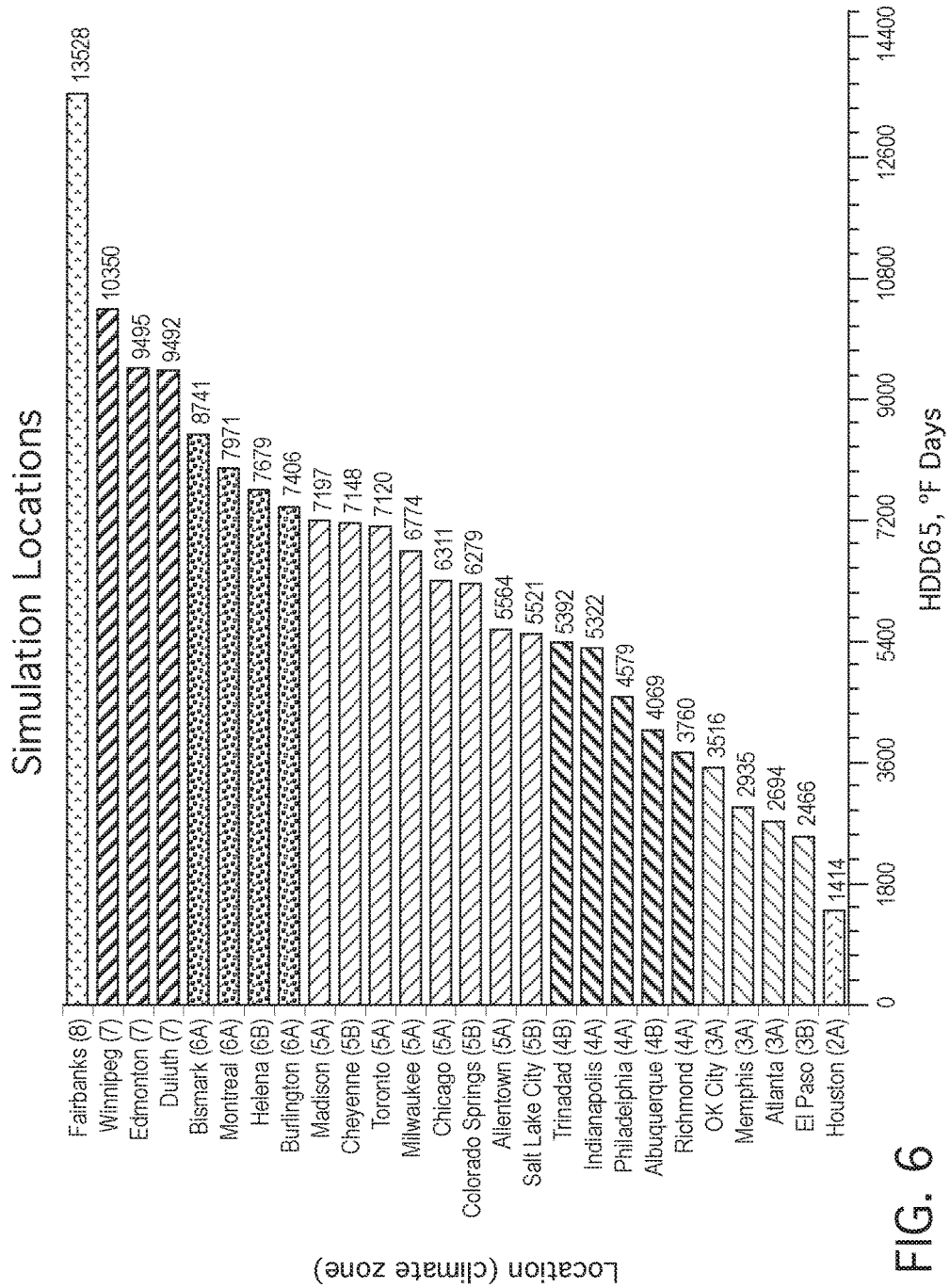
FIG. 6 is a table listing the 26 locations spanning Climate Zones 2-8, and their respective HDD65 values, for which energy performance assessments were performed on the Medium Office Prototype Model as described in Example 8.

The energy performance assessments were performed on the Medium Office Prototype Model in the 26 locations spanning Climate Zone 2-8 that are identified in FIG. 6. The specific model used was a fully ASHRAE 90.1-2013 minimum compliant building for the Climate Zone in which it is located except for the roof surface in Climate Zone 3 (R-5 over minimum) and Climate Zones 7 & 8 (R-5 under minimum). The roof surface included 5.2 inches (132 mm) of Polyiso-R30 based on advertised values. There were three (3) simulation scenarios conducted for each location each with their respective thermal characterization profiles inputted: Constant K, Example 3 Profile, and Example 7 Profile. The simulations were conducted in each case using EnergyPlus by selecting the advanced surface conduction algorithm called "Conduction Finite Difference" (CFD). For the 5.2 inches (132 mm) of Polyiso roof insulation, there were eleven (11) nodes and ten (10) layers at 0.52 inches (13.2 mm) per layer. Node temperature was the critical output result required and the data was organized on an hourly basis (8,760 hours in a year). The mean temperature of each layer was calculated from the average of the two (2) node temperatures and from this value the corresponding layer R-value was determined. The R-values from the ten (10) layers were summed and the total R-value of the insulation for each hour was recorded. The mean temperature for the entire insulation was determined by averaging the mean temperatures of the ten (10) layers. The Delta T ($\Delta T$) across the insulation was calculated by subtracting the exterior insulation node temperature from the interior insulation node temperature. Finally, a calculated average heat transfer rate (Q) across the insulation was determined by dividing the Delta T by the R-value. The following results were recorded for each hour for the insulation surface: Mean Temperature ($M_T$), R-value (R), Delta T ($\Delta T$), and Calculated Average Rate of Heat Conduction (Q).

Having the hourly results available in order to calculate the Heat Loss Weight R-value, the following steps were performed: (1) The months of the year in which the heating costs are at least 95% of the annual heating costs was determined and the data pared such that all other months were deleted; (2) The remaining data was sorted by Delta T and the hours that had a positive Delta T value were deleted so that only the heat loss hourly events remained; (3) The remaining data was sorted by mean temperature and all hourly events that had a mean temperature of 65° F. or greater were deleted; (4) The remaining mean temperature results were grouped in bins with intervals of 2° F.; (5) For hourly events in each bin, the average R-value was determined and the sum of the Calculated Average Rate of Heat Conduction values was determined; (6) the grand total Q was derived by summing the bins' total Q and calculating each bin weight fraction by dividing its Total Q by the Grand Total Q (the sum of all bin weight fractions must equal 1.0); and (7) each bin's average R-value was multiplied by the weight fraction previously derived and these values added to provide a Heat Loss Weighted R-value.

By way of example, for Chicago Medium Office, the number of events (count) with heating criteria of $\Delta T<0$ and Avg. $T_M$ of layers<65° F. (18.3° C.) was 3196 hrs. Using a typical hour (mid-February at 8 am) with outdoor air temperature of 31° F. (−0.6° C.), the insulation node temperatures ° F. (° C.) for insulation produced according to Example 7 are set forth in Table 11.

TABLE 11

| Node 2 | Node 3 | Node 4 | Node 5 | Node 6 | Node 7 | Node 8 | Node 9 | Node 10 | Node 11 | Node 12 |
| --- | --- | --- | --- | --- | --- | --- | --- | --- | --- | --- |
| 32.38 | 33.30 | 35.18 | 37.77 | 40.89 | 44.40 | 48.25 | 52.33 | 56.47 | 60.61 | 64.72 |
| (0.2) | (0.7) | (1.8) | (3.2) | (4.9) | (6.9) | (9.0) | (11.3) | (13.6) | (15.9) | (18.2) |

The insulation layer mean temperatures ° F. (° C.) for insulation produced according to Example 7 are set forth in Table 12.

TABLE 12

| 2/3 | 3/4 | 4/5 | 5/6 | 6/7 | 7/8 | 8/9 | 9/10 | 10/11 | 11/12 |
|---|---|---|---|---|---|---|---|---|---|
| 32.84 (0.5) | 34.24 (1.2) | 36.48 (2.5) | 39.33 (4.1) | 42.64 (5.9) | 46.32 (8.0) | 50.29 (10.2) | 54.40 (12.4) | 58.54 (14.7) | 62.67 (17.0) |

The calculated heat-loss weight R-value for insulation produced according to Example 7 is set forth in Table 13.

TABLE 13

| Bin # | Bin Midpoint | Avg $T_M$ (layers), °F. (°C.) Bin Minimum | Count | Bin Avg. | Total R-value, °F.·ft$^2$·h/Btu Average | Weighted | Calculated Steady State Q (ΔT/R by event) Btu/ft$^2$·h Sum | Weighted |
|---|---|---|---|---|---|---|---|---|
| 1 | 14 (−10) | 13 (10.6) | 0 | — | — | — | — | — |
| 2 | 16 (−8.9) | 15 (−9.4) | 4 | 16.63 | 28.63 | 0.07 | −11.05 | 0.0026 |
| 3 | 18 (−7.8) | 17 (−8.3) | 16 | 18.04 | 28.69 | 0.30 | −43.93 | 0.0104 |
| 4 | 20 (−6.7) | 19 (−7.2) | 24 | 19.94 | 28.78 | 0.44 | −64.54 | 0.0153 |
| 5 | 22 (−5.6) | 21 (−6.1) | 21 | 22.07 | 28.90 | 0.38 | −55.83 | 0.0132 |
| 6 | 24 (−4.4) | 23 (−5) | 35 | 24.05 | 29.04 | 0.60 | −86.80 | 0.0206 |
| 7 | 26 (−3.3) | 25 (−3.9) | 58 | 25.88 | 29.16 | 0.94 | −135.91 | 0.0322 |
| 8 | 28 (−2.2) | 27 (−2.8) | 55 | 28.13 | 29.35 | 0.84 | −121.15 | 0.0287 |
| 9 | 30 (−1.1) | 29 (−1.7) | 59 | 30.04 | 29.52 | 0.84 | −120.11 | 0.0285 |
| 10 | 32 (0) | 31 (−0.6) | 109 | 32.07 | 29.66 | 1.52 | −216.22 | 0.0512 |
| 11 | 34 (1.1) | 33 (0.6) | 93 | 34.00 | 29.80 | 1.24 | −175.71 | 0.0416 |
| 12 | 36 (2.2) | 35 (1.7) | 123 | 36.01 | 29.95 | 1.54 | −216.48 | 0.0513 |
| 13 | 38 (3.3) | 37 (2.8) | 156 | 38.01 | 30.06 | 1.84 | −258.15 | 0.0611 |
| 14 | 40 (4.4) | 39 (3.9) | 162 | 40.11 | 30.14 | 1.90 | −266.01 | 0.0630 |
| 15 | 42 (5.6) | 41 (5) | 196 | 42.02 | 30.21 | 2.15 | −300.78 | 0.0712 |
| 16 | 44 (6.7) | 43 (6.1) | 260 | 44.01 | 30.28 | 2.67 | −371.67 | 0.0880 |
| 17 | 46 (7.8) | 45 (7.2) | 275 | 45.90 | 30.33 | 2.64 | −366.78 | 0.0869 |
| 18 | 48 (8.9) | 47 (8.3) | 255 | 47.98 | 30.38 | 2.26 | −314.00 | 0.0744 |
| 19 | 50 (10) | 49 (9.4) | 213 | 50.00 | 30.44 | 1.73 | −239.41 | 0.0567 |
| 20 | 52 (11.1) | 51 (10.6) | 208 | 51.98 | 30.46 | 1.61 | −222.93 | 0.0528 |
| 21 | 54 (12.2) | 53 (11.7) | 153 | 53.93 | 30.48 | 1.07 | −148.17 | 0.0351 |
| 22 | 56 (13.3) | 55 (12.8) | 162 | 56.05 | 30.44 | 1.02 | −141.38 | 0.0335 |
| 23 | 58 (14.4) | 57 (13.9) | 156 | 57.92 | 30.38 | 0.88 | −121.90 | 0.0289 |
| 24 | 60 (15.6) | 59 (15) | 153 | 60.03 | 30.28 | 0.70 | −97.38 | 0.0231 |
| 25 | 62 (16.7) | 61 (16.1) | 150 | 62.05 | 30.14 | 0.58 | −80.60 | 0.0191 |
| 26 | 64 (17.8) | 63 (17.2) | 100 | 63.93 | 29.99 | 0.32 | −44.89 | 0.0106 |
| | | | | | Heat Loss Weighted R-value | 30.05 5.779 (1.002) | −4222 | 1.0 |

Figure 7:
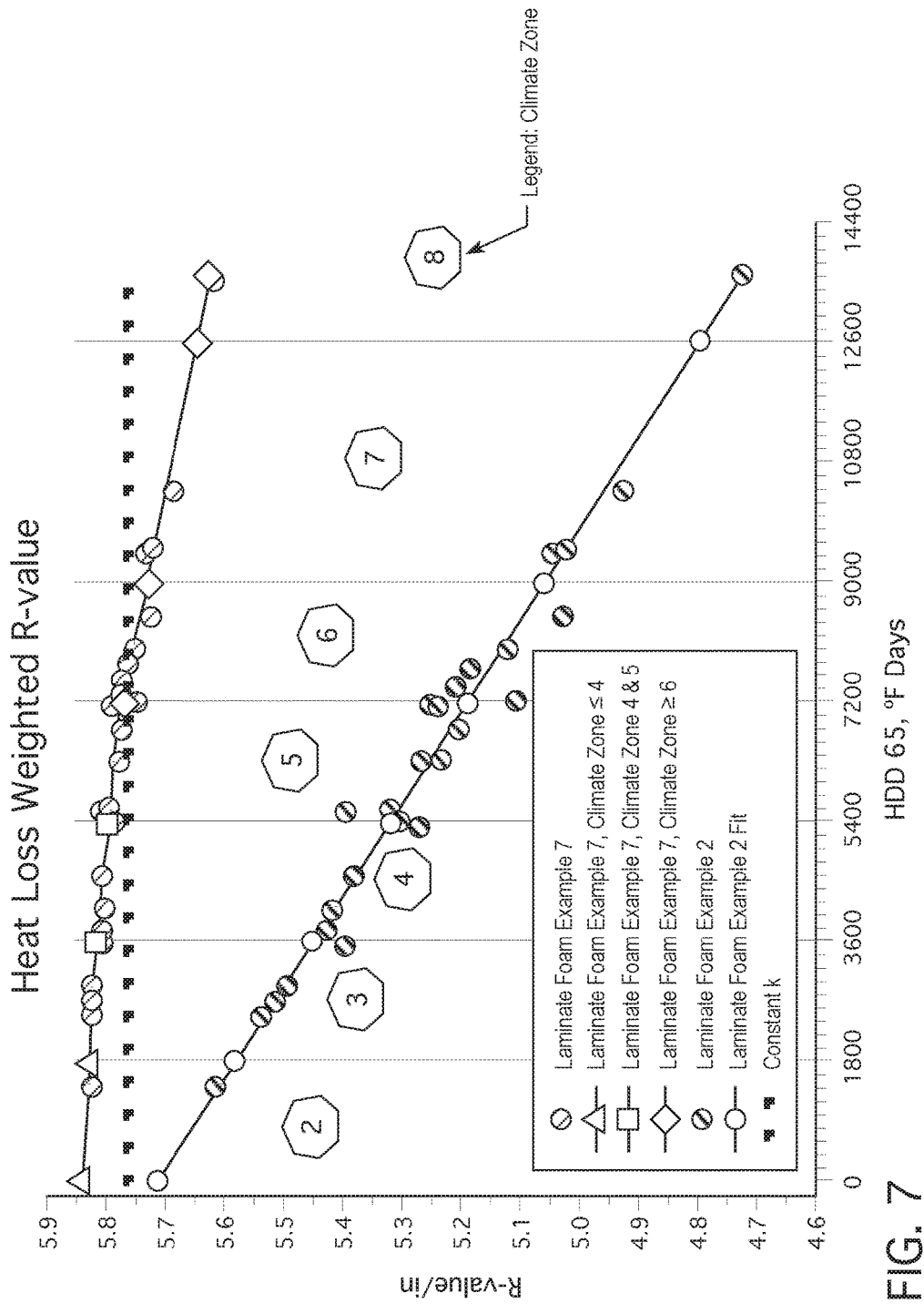
FIG. 7 is a graphical representation of the calculated heat-loss weight R-values at various locations determined as described in Example 8.

As previously mentioned, the above-described assessment was conducted in the 26 locations spanning Climate Zone 2-8 (see FIG. 6) and using the thermal characterization profiles for Constant K, Example 3 Profile, and Example 7 Profile. The results are summarized in FIG. 7.

Example 9: Preparation of the Second Polyisocyanurate Foam-Forming Composition and Polyisocyanurate Faced Foam Laminate with n-Pentane A polyisocyanuarate foam-forming composition was prepared using the components and amounts (in parts by weight) listed in Table 14 in which a blowing agent composition contained only n-pentane for the purpose of making a foam where the onset of condensation would be expected to occur above 40° F. (4.4° C.) with 4.71% n-pentane based on Table 8. The NCO and POLYOL where used in relative amount to provide an isocyanate index (ratio of the equivalent amount of isocyanate used relative to the theoretical equivalent of one equivalent isocyanate per one equivalent of hydroxyl) of 2.50.

TABLE 14

| Component | Amount |
|---|---|
| POLYOL[1] | 28.39 |
| Fyrol ® PCF[2] | 2.84 |
| Surfactant[3] | 0.71 |
| Dabco ® K-15[4] | 1.63 |
| Polycat ® 46[5] | 0.21 |
| PMDETA[6] | 0.066 |
| Water | 0.42 |
| n-Pentane | 4.71 |
| NCO[7] | 61.0 |

[1]Stepanpol ® PS-2352 polyester polyol having a functionality of 2 and an OH Value of 235 which is commercially available from the Stepan Company.
[2]an alkyl phosphate flame retardant based on Tris(2-chloroisopropyl) phosphate commercially available from ICL-Supresta
[3]Tegostab B8513, which is commercially available from Evonik Industries.
[4]Potassium octoate commercially available from Air Products Company.
[5]Potassium acetate commercially available from Air Products Company.
[6]Pentamethyldiethylenetriamine catalyst commercially available from Air Products Company.
[7]Polymeric MDI which is commercially available under the name Mondur ® 489 from Covestro LLC.

A polyisocyanurate faced foam laminate based on this composition was prepared using the equipment and procedure described in Example 2 and LTTR measurements were conducted in accordance with S770-09 using the procedure of Example 3 to define mathematical correlations that provide LTTR values at different temperatures.

The foam met standard foam physical properties requirements for Type II products in accordance with ASTM C 1289, Standard Specification for Faced Rigid Cellular Polyisocyanurate Thermal Insulation Board. Additional physical properties are listed in Table 15.

TABLE 15

| Property | Result |
|---|---|
| Core Density | 1.63 lb/ft³ (26.1 kg/m³) |
| Thickness | 2.52 inches (63.75 millimeters) |

Figure 8:
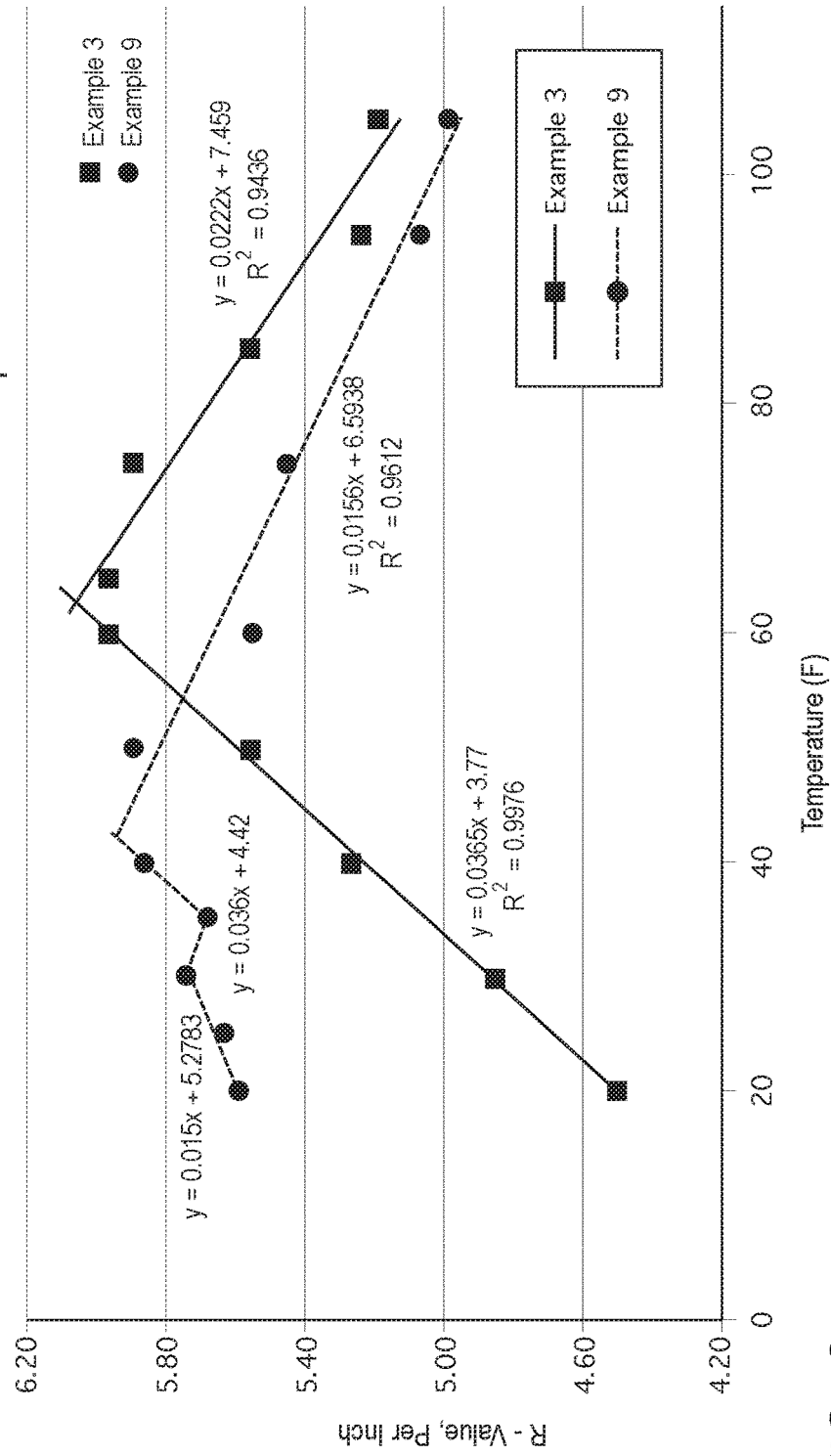
FIG. 8 is a graphical representation of the LTTR measurements conducted in Example 9, which includes mathematical equations determined by a linear fit of the data.

It was surprisingly observed again that a single cold side liquid line did not describe liquid condensation for this formulation comprised of a single hydrocarbon blowing agent. There are two inflection points observed in the foam at about 52° F. (11.11° C.) and at about 30° F. (−1.11° C.) with the higher temperature value presumed to correspond to the onset of condensation of water vapor in the cell gas. The laboratory environment in which the foam slices were conditioned was kept at 70° F. (21.11° C.) and at about 50% relative humidity in accordance with CAN/UL S770-09. If a similar relative humidity existed in the cell gas, then the dew point for water condensation would be about 50.5° F. (10.28° C.) and that process would offset the normal improvement in LTTR at lower temperatures until all water vapor in the cell had condensed, which occurred at about 35° F. (1.67° C.). Below that temperature, the LTTR values correspond to the "true" cold side line for n-pentane condensation in the second polyisocyanurate faced foam laminate. The inflection point for the intersection of the "true" cold side line and the warm side line for 4.71% n-pentane in the foam is 42.9° F. (3.85° C.) based on the linear regressions for the two lines. All LTTR values for the second polyisocyanurate faced foam laminate made with n-pentane were greater than 5.4 ft²·hr·° F./Btu·inch (0.936 m²·° C./W@25 mm) in the temperature range of 20° F. (−6.7° C.) to 75° F. (23.9° C.) despite onset of condensation occurring at about 52° F. (11.11° C.), as is illustrated in FIG. 8.

This specification has been written with reference to various non-limiting and non-exhaustive embodiments. However, it will be recognized by persons having ordinary skill in the art that various substitutions, modifications, or combinations of any of the disclosed embodiments (or portions thereof) may be made within the scope of this specification. Thus, it is contemplated and understood that this specification supports additional embodiments not expressly set forth herein. Such embodiments may be obtained, for example, by combining, modifying, or reorganizing any of the disclosed steps, components, elements, features, aspects, characteristics, limitations, and the like, of the various non-limiting embodiments described in this specification. In this manner, Applicant(s) reserve the right to amend the claims during prosecution to add features as variously described in this specification, and such amendments comply with the requirements of 35 U.S.C. § 112, first paragraph, and 35 U.S.C. § 132(a).

What is claimed is:

1. A method for designing a polyisocyanurate foam-forming composition, comprising:
    (a) measuring the LTTR of a first polyisocyanurate faced foam laminate prepared from a first polyisocyanurate foam-forming composition comprising a blowing agent composition comprising one or more hydrocarbon blowing agents with an atmospheric pressure boiling point of at least 68° F. (20° C.), wherein the LTTR is measured according to CAN/UL S770-09 at a plurality of temperatures to identify a calculated inflection point temperature below which defines a first mathematical correlation between temperature and the LTTR of the first polyisocyanurate faced foam laminate and above which defines a second mathematical correlation between temperature and the LTTR of the first polyisocyanurate faced foam laminate;
    (b) identifying a plurality of predicted mathematical correlations between temperature and the LTTR of the first polyisocyanurate faced foam laminate at a plurality of reduced inflection point temperatures below the calculated inflection point temperature;
    (c) using the plurality of predicted mathematical correlations to design a second polyisocyanurate foam-forming composition that is different from the first polyisocyanurate foam-forming composition and which comprises a blowing agent composition comprising one or more hydrocarbon blowing agents with an atmospheric pressure boiling point of at least 68° F. (20° C.), wherein the second polyisocyanurate foam-forming composition produces a second polyisocyanurate faced foam laminate that has a LTTR of at least 5.4 ft²·hr·° F./BTU·inch (0.936 mm) at all mean insulation temperatures within a temperature range of 10° F. to 75° F. (−12.2° C. to 23.9° C.), when measured according to CAN/UL S770-09; and
    (d) preparing the second polyisocyanurate foam-forming composition comprising the second blowing agent composition;
    wherein the step of identifying a plurality of predicted mathematical correlations between temperature and the LTTR of the first polyisocyanurate faced foam laminate at a plurality of reduced inflection point temperatures below the calculated inflection point temperature comprises defining estimated cold side lines at a plurality of reduced inflection point temperatures;
    wherein the defining estimated cold side lines at a plurality of reduced inflection point temperatures comprises using a selected reduced inflection point temperature to calculate LTTR using a warm side line defined by a linear regression fit of the measured LTTR's of the first polyisocyanurate faced foam laminate, wherein the warm side line is defined by the Equation:

$$Y_{calc} = (m_w \cdot x) + b_w,$$

in which $Y_{calc}$ is LTTR in ft²·hr·° F./BTU·inch; x is the selected reduced inflection point temperature in ° F., and $m_w$ and $b_w$ are values defined by the linear regression fit in which $m_w$ defines the slope of the warm side line of the linear regression fit and $b_w$ defines the LTTR axis intercept value of the warm side line of the linear regression fit;
    further comprising using the calculated LTTR to determine a calculated y-intercept "b" of a calculated cold side line at the selected reduced inflection point temperature by using the equation:

$$b_{c\text{-}calc} = Y_{calc} - (m_c \cdot X)$$

in which $Y_{calc}$ is the calculated LTTR in ft²·hr·° F./BTU·inch; x is the selected reduced inflection point temperature in ° F.; $m_c$ is the slope of the cold side line of the linear regression fit; and $b_{c\text{-}calc}$ is the calculated y-intercept "b" of the calculated cold side line at the selected reduced inflection point temperature.

2. The method of claim 1, wherein the first polyisocyanurate foam-forming composition comprises an organic polyisocyanate comprising polymeric diphenylmethane diisocyanate (pMDI).

3. The method of claim 2, wherein the first polyisocyanurate foam-forming composition comprises a material having at least two reactive groups capable of reacting with an isocyanate group and comprising a polyester polyol.

4. The method of claim 1, wherein the first polyisocyanurate foam-forming composition comprises a blowing agent composition comprising one or more hydrocarbon blowing agents with an atmospheric pressure boiling point of at least 68° F. (20° C.) and water.

5. The method of claim 4, wherein the first polyisocyanurate foam-forming composition comprises a blowing agent composition comprising one or more hydrocarbon blowing agents with an atmospheric pressure boiling point of at least 68° F. (20° C.) comprising n-pentane.

6. The method of claim 1, wherein the first polyisocyanuarate faced foam laminate has a core foam density of 1.50 to 1.80 lb/ft$^3$ (24.0 to 28.8 kg/m$^3$).

7. The method of claim 1, wherein the LTTR of the first polyisocyanurate faced foam laminate is measured in accordance with CAN/UL S770-09 at (i) at least 3 temperatures within the range of 20° F. to less than 75° F. (−6.7° C. to less than 23.9° C.), and (ii) at least 3 temperatures within the range of 75° F. to 105° F. (23.9° C. to 40.6° C.).

8. The method of claim 1, wherein the LTTR of the first polyisocyanurate faced foam laminate is less than 5.4 ft$^2$·hr·° F./BTU·inch (0.936 m$^2$·° C./W@25 mm) at temperatures with the range of 10° F. to 40° F. (−12.2° C. to 4.44° C.).

9. The method of claim 1, wherein the step of designing a second polyisocyanurate foam-forming composition comprises using the plurality of estimated mathematical correlations between temperature and the LTTR of the first polyisocyanurate faced foam laminate at a plurality of temperatures below the calculated inflection point temperature to determine a predicted inflection point temperature range where heating energy consumption of a selected building type in geographic locations where HDD65 values are greater than 2000 that is insulated with a polyisocyanurate foam insulation would be equal to or lower than the heating energy consumption for the selected building type in the same geographic location that is insulated with a theoretical insulation having a selected constant LTTR at all temperatures within the range of 10° F. to 75° F. (−12.2° C. to 23.9° C.).

10. The method of claim 9, wherein the selected constant LTTR is 5.77 ft$^2$·hr·° F./BTU·inch (1.00 m$^2$·° C./W@25 mm).

11. The method of claim 10, wherein the step of determining a predicted inflection point temperature range where heating energy consumption of a selected building type in geographic locations where HDD65 values are greater than 2000 that is insulated with a polyisocyanurate foam insulation would be equal to or lower than the heating energy consumption for the selected building type in the same geographic location that is insulated with a theoretical insulation having a selected constant LTTR at all temperatures within the range of 10° F. to 75° F. (−12.2° C. to 23.9° C.), comprises using a whole building energy simulation program in which a conduction finite difference algorithm is used to examine heat transfer across surfaces.

12. The method of claim 11, wherein the predicted inflection point temperature range is 30° F. (−1.1° C.) to 40° F. (4.4° C.).

13. The method of claim 12, wherein the step of designing of the second polyisocyanurate foam-forming composition comprises:
(1) determining a mass of blowing agent needed to make a foam of a selected mass and having a preselected target foam density using the Antoine equation;
(2) determining the total volume occupied by the solid component of the selected mass of foam and subtracting this amount from the total volume to obtain an estimated volume of space that contains the blowing agent at the saturation vapor pressure of the blowing agent;
(3) calculating the maximum mass of a selected blowing agent that can be used to produce a foam having the preselected target inflection point temperature using the Ideal Gas law;
(4) repeating steps (1)-(3) for any hydrocarbon blowing agent of interest for use in the second polyisocyanurate foam-forming composition; and
(5) selecting a hydrocarbon blowing agent composition in which the total mass of hydrocarbon blowing agent is at or below the maximum amount of such blowing agent that can be used to avoid condensation of the blowing agent above the target inflection point temperature.

14. The method of claim 1, further comprising preparing a second polyisocyanurate faced foam laminate from the second polyisocyanurate foam-forming composition.

15. The method of claim 14, further comprising measuring the LTTR of the second polyisocyanurate face foam laminate in accordance with CAN/UL S770-09 at (i) at least 3 temperatures less in the range of 20° F. (−6.7° C.) to less than 75° F. (23.9° C.), and (ii) at least 3 temperatures in the range of 75° F. to 105° F. (23.9° C. to 40.6° C.).

16. The method of claim 15, further comprising assessing whether the second faced foam laminate has a calculated heat-loss weighted R-value greater than 5.5 ft$^2$·hr·° F./BTU·inch in locations where HDD65 values are greater than 2000.

17. A method for designing a polyisocyanurate foam-forming composition, comprising:
(a) measuring the LTTR of a first polyisocyanurate faced foam laminate prepared from a first polyisocyanurate foam-forming composition comprising a blowing agent composition comprising one or more hydrocarbon blowing agents with an atmospheric pressure boiling point of at least 68° F., wherein the LTTR is measured according to CAN/UL S770-09 at a plurality of temperatures to identify a calculated inflection point temperature below which defines a first mathematical correlation between temperature and the LTTR of the first polyisocyanurate faced foam laminate and above which defines a second mathematical correlation between temperature and the LTTR of the first polyisocyanurate faced foam laminate;
(b) identifying a plurality of predicted mathematical correlations between temperature and the LTTR of the first polyisocyanurate faced foam laminate at a plurality of reduced inflection point temperatures below the calculated inflection point temperature;
(c) using the plurality of predicted mathematical correlations to determine a predicted inflection point temperature where energy consumption of a selected building type insulated with a polyisocyanurate foam insulation would be equal to or lower than the energy consumption for the selected building type when insulated with a theoretical insulation having a constant LTTR of 5.77 ft²·hr·° F./BTU·inch at all temperatures within the range of 10° F. to 75° F.;
(d) using the predicted inflection point temperature to design a second polyisocyanurate foam-forming composition that is different from the first polyisocyanurate foam-forming composition and which comprises a blowing agent composition comprising one or more hydrocarbon blowing agents with an atmospheric pressure boiling point greater than or equal to 20° C., wherein the second polyisocyanurate foam-forming composition produces a second polyisocyanurate faced foam laminate that has a LTTR of at least 5.4 ft²·hr·° F./BTU·inch at all mean insulation temperatures within a temperature range of 10° F. to 75° F., when measured according to CAN/UL S770-09; and
(e) preparing the second polyisocyanurate foam-forming composition comprising the second blowing agent composition;
wherein the step of identifying a plurality of predicted mathematical correlations between temperature and the LTTR of the first polyisocyanurate faced foam laminate at a plurality of reduced inflection point temperatures below the calculated inflection point temperature comprises defining estimated cold side lines at a plurality of reduced inflection point temperatures;
wherein the defining estimated cold side lines at a plurality of reduced inflection point temperatures comprises using a selected reduced inflection point temperature to calculate LTTR using a warm side line defined by a linear regression fit of the measured LTTR's of the first polyisocyanurate faced foam laminate, wherein the warm side line is defined by the Equation:

$$Y_{calc} = (m_w \cdot x) + b_w,$$

in which $Y_{calc}$ is LTTR in ft²·hr·° F./BTU·inch; x is the selected reduced inflection point temperature in ° F., and $m_w$ and $b_w$ are values defined by the linear regression fit in which $m_w$ defines the slope of the warm side line of the linear regression fit and $b_w$ defines the LTTR axis intercept value of the warm side line of the linear regression fit;

further comprising using the calculated LTTR to determine a calculated y-intercept "b" of a calculated cold side line at the selected reduced inflection point temperature by using the equation:

$$b_{c\text{-}calc} = Y_{calc} - (m_c \cdot x)$$

in which $Y_{calc}$ is the calculated LTTR in ft²·hr·° F./BTU·inch; x is the selected reduced inflection point temperature in ° F.; $m_c$ is the slope of the cold side line of the linear regression fit; and $b_{c\text{-}calc}$ is the calculated y-intercept "b" of the calculated cold side line at the selected reduced inflection point temperature.

18. The method of claim 17, further comprising:
(f) preparing the second polyisocyanurate faced foam laminate from the second polyisocyanurate foam-forming composition, wherein the second polyisocyanurate faced foam laminate has a calculated heat-loss weighted R-value greater than 5.5 ft²·hr·° F./BTU·inch in locations where HDD65 values are greater than 2000.

19. The method of claim 17, wherein the LTTR of the first polyisocyanurate faced foam laminate is measured in accordance with CAN/UL S770-09 at: (i) at least 3 temperatures within the range of 20° F. to less than 75° F. (−6.7° C. to less than 23.9° C.), and (ii) at least 3 temperatures within the range of 75° F. to 105° F. (23.9° C. to 40.6° C.).

* * * * *